United States Patent
Beard et al.

[11] Patent Number: 6,127,382
[45] Date of Patent: Oct. 3, 2000

[54] AMINES SUBSTITUTED WITH A TETRAHYDROQUINOLINYL GROUP AN ARYL OR HETEROARYL GROUP AND AN ALKYL GROUP, HAVING RETINOID-LIKE BIOLOGICAL ACTIVITY

[75] Inventors: Richard L. Beard, Newport Beach; Raok Jeon, Irvine; Diana F. Colon, Newport Beach; Roshantha A. Chandraratna, Mission Viejo, all of Calif.

[73] Assignee: Allergan Sales, Inc., Irvine, Calif.

[21] Appl. No.: 09/375,846

[22] Filed: Aug. 16, 1999

[51] Int. Cl.$^7$ .................. A61K 31/47; C07D 401/00; C07D 215/16; C07D 215/00; C07D 215/20

[52] U.S. Cl. .................. 514/311; 514/252; 514/253; 514/254; 514/312; 514/314; 544/238; 544/405; 546/158; 546/165

[58] Field of Search .................. 514/252, 253, 514/254, 311, 312, 314; 544/238, 405; 546/158, 165

[56] References Cited

U.S. PATENT DOCUMENTS

| | | | |
|---|---|---|---|
| 4,826,984 | 5/1989 | Berlin et al. | 546/134 |
| 5,037,755 | 8/1991 | Burr et al. | 435/210.27 |
| 5,399,561 | 3/1995 | Chandraratna | 514/252 |
| 5,455,265 | 10/1995 | Chandraratna | 514/448 |
| 5,498,755 | 3/1996 | Chandraratna | 564/272 |
| 5,556,996 | 9/1996 | Beard et al. | 549/407 |
| 5,602,130 | 2/1997 | Chandraratna | 514/247 |
| 5,616,712 | 4/1997 | Teng et al. | 546/158 |
| 5,663,347 | 9/1997 | Chandraratna | 546/152 |
| 5,672,710 | 9/1997 | Beard et al. | 548/188 |
| 5,677,323 | 10/1997 | Chandraratna | 514/374 |
| 5,717,094 | 2/1998 | Chandraratna | 544/238 |
| 5,739,338 | 4/1998 | Beard et al. | 546/153 |
| 5,817,836 | 10/1998 | Vuligonda et al. | 549/23 |
| 5,856,490 | 1/1999 | Teng et al. | 546/165 |
| 5,877,207 | 3/1999 | Klein et al. | 514/546 |

FOREIGN PATENT DOCUMENTS

| | | | |
|---|---|---|---|
| 0130795 | 1/1985 | European Pat. Off. | C07D 311/58 |
| 0350846 | 1/1990 | European Pat. Off. | C07D 311/58 |
| 94 05019 | 10/1995 | France | C07C 63/64 |
| 3316932 | 11/1983 | Germany | C07D 311/58 |
| 93/11755 | 6/1993 | WIPO | A61K 31/07 |
| 93/21146 | 10/1993 | WIPO | C07C 69/76 |
| 95/04036 | 2/1995 | WIPO | C07C 403/20 |
| 98/45242 | 10/1998 | WIPO | C07C 63/49 |

OTHER PUBLICATIONS

Chemical abstracts 110:231627, abstract of EP290153 and US Pat #4898872, 1988.
Chemical abstracts 110:23516, abstract of JP63132864, 1988.
Dawson and William H. Okamura, *Chemistry and Biology of Synthetic Retinoids*, published by CRC Press, Inc., 1990, pp. 334–335.
Verma & Boutwell, Cancer Research, (1977), 37, 2196–2201.
Cancer Research: 1662–1670 (1975).
Feigner P. L. and Holm M. (1989) Focus, 112.
Heyman et al., Cell 68, 397–406 (1992).
Klein et al., J. Biol. Chem. 271,22692–22696 (1996).
Chen et al. (1987) Mol. Cell. Biol. 7,2745–2752.
de Wet (1987) Mol. Cell. Biol. 7, 725–737.
Nagpal et al., EMBO J. 12, 2349–2360 (1993).
Corey, E. J., Schmidt, G., *Tet. Lett.*, 399 (1979).
Omura, K., Swern, D., *Tetrahedron*, 1978, 34, 1651.

*Primary Examiner*—D. Margaret Seaman
*Attorney, Agent, or Firm*—Gabor L. Szekeres; Robert J. Baran; Martin A. Voet

[57] ABSTRACT

Compound of Formula 1

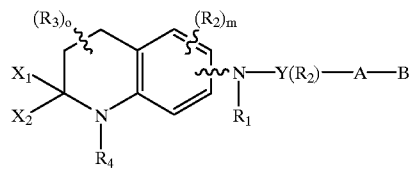

where the symbols have the meaning described in the specification, have retinoid-like biological activity.

38 Claims, No Drawings

AMINES SUBSTITUTED WITH A TETRAHYDROQUINOLINYL GROUP AN ARYL OR HETEROARYL GROUP AND AN ALKYL GROUP, HAVING RETINOID-LIKE BIOLOGICAL ACTIVITY

BACKGROUND OF THE INVENTION

1. Field of the Invention

The present invention relates to novel compounds having retinoid-like biological activity. More specifically, the present invention relates to amines substituted with a tetrahydroquinolinyl group, an aryl or heteroaryl group and an alkyl group, which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject.

Among United States and foreign patents which disclose compounds having retinoid agonist, antagonist or inverse agonist like biological activity and are known to applicant the following examples include diaryl or heteroaryl substituted amines and are therefore of interest as background to the present invention: WO9845242-A1, published on Oct. 15, 1998, and French patent application number 94 05019, laid-over-to-public-inspection on Oct. 27, 1995.

Among the numerous United States and foreign patents which disclose compounds having retinoid agonist, antagonist or inverse agonist like biological activity and are known to applicant the following examples include a tetrahydroquinoline or tetrahydroquinolinone ring structure and are therefore of interest as background to the present invention: U.S. Pat. No. 5,616,712 (ethynyl compounds substituted with an aryl or heteroaryl group and with a tetrahydroquinoline-2-one or 2-thione derivative); U.S. Pat. No. 5,739,338 (tetrahydroquinoline and tetrahydroquinoline-2-one derivatives having the ring nitrogen substituted with an aryl or heteroaryl group); and U.S. Pat. Nos. 5,856,490; 5,817,836; 5,663,347; 5,672,710; 5,677,323; 5,717,094; 5,556,996; 5,602,130; 5,399,561; 5,498,755; 4,826,984; 5,037,755; published PCT applications WO 93/21146; WO/95/04036; published European applications or patents EPO 0 130 795; EPO 0 350 846; and German Offenlegungsschrift DE 3316932 A1.

SUMMARY OF THE INVENTION

The present invention relates to compounds of Formula 1

Formula 1

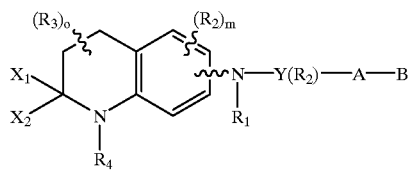

where $X_1$ and $X_2$ independently are H, or alkyl of 1 to 6 carbons, or F, or the $X_1$ and $X_2$ groups jointly symbolize an oxo (=O) or thio (=S) function;

$R_1$ is H, alkyl of 1 to 10 carbons, phenyl-$C_1$–$C_6$ alkyl, $C_1$–$C_6$-alkylphenyl, heteroaryl-$C_1$–$C_6$ alkyl, $C_1$–$C_6$-alkylheteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

$R_2$ is independently H, alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer having the values of 0 to 3;

$R_3$ is independently H, alkyl of 1 to 6 carbons, or F;

o is in an integer having the values of 0 to 4;

$R_4$ is H, alkyl of 1 to 10 carbons, phenyl, naphthyl, phenyl-$C_1$–$C_6$-alkyl, naphthyl-$C_1$–$C_6$-alkyl, heteroaryl selected from a group consisting of pyridyl, thienyl, furyl, pyridazinyl, pyrimidinyl, pyrazinyl, thiazolyl, oxazolyl, imidazolyl and pyrrazolyl, or heteroaryl-$C_1$–$C_6$-alkyl, said phenyl, naphthyl and heteroaryl groups being optionally substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, or $COOR_1$;

Y is a phenyl or naphthyl group, or heteroaryl selected from a group 5consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of metabolic diseases such as type II non-insulin dependent diabetes mellitus (NIDDM) and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

Generally speaking, the second aspect of the invention relates to the use of the novel compounds to prevent or treat diseases and conditions which are responsive to compounds that promote the expression of or bind to receptors belonging to the steroid or thyroid receptor superfamily.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

Biological Activity, Modes of Administration
Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and a decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670, 1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested. These assays are expected to demonstrate that the compounds of the present invention act as agonists of one or more of the above-described receptors.

However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4\times10^5$ cells/well) were transiently transfected with the luciferase reporter plasmid MTV-4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference. In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. EMBO J. 12, 2349–2360 (1993) expressly incorporated herein by reference. Retinoid inverse agonists are able to inhibit the basal luciferase activity in these cells in a dose dependent manner and $IC_{50}$s measured. A detailed description of the tests used for determining whether or not a compound is a retinoid antagonist or inverse agonist, and the manner of utilizing retinoid antagonists and inverse agonists is provided in U.S. Pat. No. 5,877,207, the specification of which is expressly incorporated herein by reference.

Table 1 discloses the activity of certain exemplary compounds of the invention in the above-described chimeric receptor transactivation assay, holoreceptor transactivation assay and a ligand binding assays. Particularly, the transactivation data pertaining to RAR receptors were obtained in the chimeric assay, and the data pertaining to transactivation of RXR receptors were obtained in the holoreceptor transactivation assay.

| COMPOUND NUMBER | RAR Trans. $EC_{50}$ (nM) RAR Bind $K_i$ (nM) | | | RXR Trans $EC_{50}$ (nM) RXR Bind $K_i$ (nM) | | |
|---|---|---|---|---|---|---|
| | α | β | γ | α | β | γ |
| 5 | NA | NA | NA | NA | NA | NA |
| | >30 k | >30 k | >30 k | 56 k | | >100 k |
| 6 | NA | NA | NA | 1 k (50) | >1 k (40) | NA |
| | 10 k | >30 k | >30 k | 9 k | | >10 k |
| 10 | NA | NA | NA | 1 k (70) | NA | 1 k (50) |
| | >10 k | >10 k | >10 k | >1 k | >1 k | >10 k |
| 12 | NA | NA | NA | 78 (134) | 1 k (75) | 148 (150) |
| | 467 | 7.9 k | 1 k | 136 | 273 | 1.3 k |
| 14 | NA | NA | NA | NA | NA | NA |
| | 340 | 7.7 k | 1.5 k | 904 | 778 | >1 k |
| 24 | NA | NA | NA | 36 (90) | 1 k (70) | 69 (117) |
| | >10 k | >10 k | 9.2 k | 448 | 1.1 k | >1 k |
| 22 | NA | NA | | 1 k (80) | >1 k (15) | 1 k (100) |
| | >10 k | >10 k | 1.7 k | 1.2 k | 1.1 k | >1 k |
| 26 | NA | NA | NA | >1 k (25) | >1 k (10) | 1 k (75) |
| | 15 k | 11 k | 4.7 k | 413 | 386 | 1.3 k |
| 38 | NA | NA | NA | 0.6 (114) | 7 (102) | 1 (109) |
| | >10 k | >10 k | 6.3 k | 10 | 57 | 27 |
| 39 | NA | NA | NA | 1 (121) | 10 (97) | 2 (112) |
| | 6.7 k | >10 k | 2.8 k | 49 | 133 | 60 |
| 40 | NA | NA | NA | 0.1 (110) | 3 (93) | 0.2 (105) |
| | 5.1 k | 24 k | 3.5 k | 9 | 42 | 34 |
| 50 | NA | NA | NA | 4 (103) | 27 (104) | 4 (102) |
| | >10 k | | >10 k | 327 | 262 | >1 k |
| 51 | NA | NA | NA | 32 (92) | 374 (119) | 47 (104) |
| | >10 k | | >10 k | 221 | 142 | 317 |
| 52 | NA | NA | NA | 0.2 (94) | 2 (96) | 0.5 (96) |
| | 9.6 k | | 10 k | 28 | 99 | 38 |
| 53 | NA | NA | NA | 0.2 (92) | 2 (93) | 0.3 (96) |
| | 3011 | | 17 k | 44 | 43 | 95 |

Numbers in parentheses indicate % efficacy relative to $10^{-6}$ M ATRA (RARs) or $10^{-6}$ M (+)-(1S,2S,1E,2E)-3-Methyl-5-[2-methyl-2-(5,5,8,8-tetramethyl-5,6,7,8-tetrahydro-naphthalen-2-yl)-cyclopropyl]penta-2,4-dienoic acid (RXRs)
NA-Not Active As it can be seen from the foregoing assay results the preferred compounds of the invention are specific or selective agonists of RXR receptors.

Modes of Administration

The compounds of this invention may be administered systemically or topically, depending on such considerations as the condition to be treated, need for site-specific treatment, quantity of drug to be administered, and numerous other considerations.

Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A usefull therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be administered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

General Embodiments and Synthetic Methodology
Definitions

The term alkyl refers to and covers any and all groups which are known as normal alkyl, branched-chain alkyl, cycloalkyl and also cycloalkylalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals often of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula— CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some compounds of the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

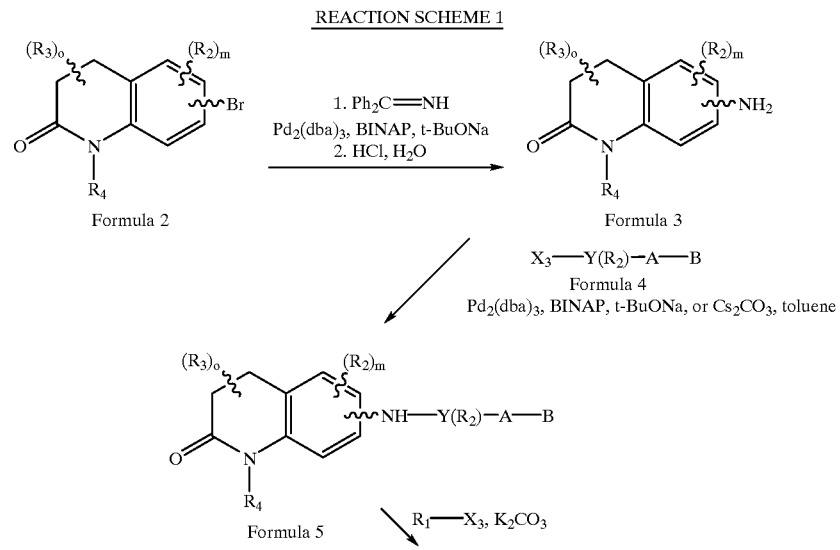

-continued

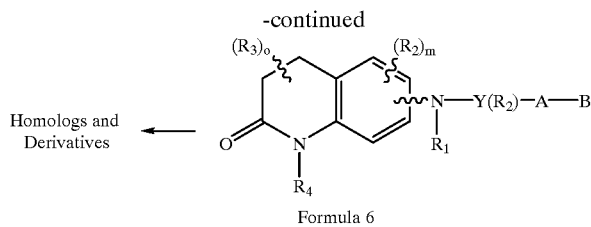

Formula 6

The compounds of the invention, can generally speaking be obtained by a series of reactions as disclosed in Reaction Schemes 1 and 2. Referring first to Reaction Scheme 1, a general method for the synthesis of compounds of Formula 1 is disclosed where, with reference to Formula 1 the symbols $X_1$ and $X_2$ jointly represent an oxo (or by analogy thio) group. The starting compound in this synthetic route is an N-alkylated, phenyl or heteroaryl substituted 6- or 7-bromo 1,2,3,4-tetrahydroquiniline-2-one of Formula 2 where the symbols $R_2$, $R_3$, and $R_4$ are defined as in connection with Formula 1. These bromo compounds can, generally speaking, be obtained in accordance with the chemical scientific and patent literature, or by such modifications of the published literature procedures which will become readily apparent to the practicing synthetic organic chemist. An example for the starting material of Formula 2 is 6-bromo-1-isopropyl-4,4-dimethyl-2-oxo-1,2,3,4-tetrahydroquinoline which can be obtained in accordance with U.S. Pat. No. 5,399,561 the specification of which is hereby incorporated by reference. Other specific examples for the starting material of Formula 2 are 7-bromo-1-isopropyl-4,4-dimethyl-2-oxo-1,2,3,4-tetrahydroquinoline and its 6-methyl analog that are synthesized in accordance with procedures that are specifically described in the experimental section of this application.

The bromo compound of Formula 2 is reacted first with benzophenone imine in the presence of tris(dibenzylideneacetone)dipalladium(0) (Pd$_2$(dba)$_3$), and (S)-(−)-2,2'-bis(diphenylphosphino)1,1'-binaphthyl (BINAP) acting as catalysts, by heating in toluene under the protective blanket of an inert gas, and then with hydrochloric acid to yield the N-alkylated or phenylated 6- or 7-amino 1,2,3,4-tetrahydroquiniline-2-one derivatives of Formula 3. The amino compounds of Formula 3 are then reacted with the reagent $X_3$—$Y(R_2)$—A—B (Formula 4) where $X_3$ represents a halogen, preferably iodine or bromine, and the remaining symbols are defined as in connection with Formula 1. The reagents of Formula 4 are halogen substituted aryl or heteroaryl compounds which, generally speaking, can be obtained by reactions well known in the art. An example of such a compound is ethyl-4-iodobenzoate which is obtainable, for example, by esterification of 4-iodobenzoic acid. This esterification reaction is described in U.S. Pat. No. 5,616,712 incorporated herein by reference. Other examples for the reagents of Formula 4 are ethyl 6-iodonicotinate (obtainable by halogen exchange reaction on 6-chloronicotinic acid followed by esterification), ethyl 5-iodo or 5-bromothiophene-2-carboxylate and ethyl 5-iodo or 5-bromofuran-2-carboxylate. The reaction of the amine compounds of Formula 3 with the halogenated reagent of Formula 4 is conducted in the presence of the catalysts tris(dibenzylideneacetone)dipalladium(0) (Pd$_2$(dba)$_3$) , and (S)-(−)-2,2'-bis(diphenylphosphino)1,1'-binaphthyl (BINAP) in the presence of an acid acceptor, such as cesium carbonate, while being heated in an inert solvent (toluene) in an inert gas atmosphere. The resulting aryl or heteroaryl N-alkyl or aryl 2-oxo-1,2,3,4-tetrahydroquinolinyl amines (disubstituted amines) of Formula 5 are within the scope of the invention, but can be converted to trisubstituted amines of Formula 6, also within the scope of the invention, by reaction with a reagent of the formula $R_1$—$X_3$ where $R_1$ is defined as in connection with Formula 1, and $X_3$ is halogen, preferably iodine or bromine. The reaction of the disubstituted amines of Formula 5 with the reagent $R_1$—$X_3$ will be recognized by those skilled in the art as an "alkylation" or analogous reaction, and is preferably conducted by heating in a solvent, such as dimethylacetamide, in the presence of an acid acceptor, such as potassium carbonate. The resulting trisubstituted amine compounds of Formula 6 include the 2-oxo-1,2,3,4-tetrahydroquinolinyl moiety and are within the scope of the invention. These compounds can be converted into further homologs and derivatives, still within the scope of the invention, by such reactions as esterification, saponification, homologation, reduction to aldehyde or alcohol stage and the like, which per se are well known in the art. These reactions usually involve transformations of the groups designated A and B in the formulas (see Formulas 1 and 6 for example) but are not necessarily limited to those. For example a transformation that involves conversion of the 2-oxo group of the tetrahydroquinolin moiety to a thione involves reaction with Lawesson's reagent, [2,4-bis(4-methoxyphenyl)-1,3-dithia-2,4-diphosphetane-2,4-disulfide]. Some of the known and published general principles and synthetic methodology employed in the transformations of the A and B groups are briefly described below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups,* Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

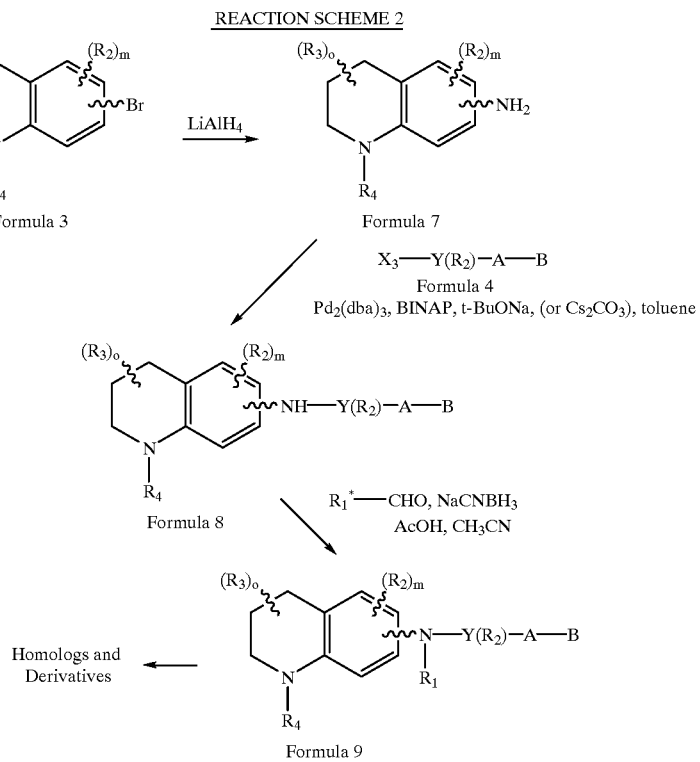

REACTION SCHEME 2

Referring now to Reaction Scheme 2, an exemplary synthetic route is described to prepare compounds of the invention where the 2-position of the tetrahydronaphthalene nucleus is unsubstituted. This reaction scheme also illustrates an alternative method for introducing the third substituent on the amino function by a reductive alkylation reaction. In accordance with this scheme, the N-alkylated or phenylated 6- or 7-amino 1,2,3,4-tetrahydroquinoline-2-one compounds of Formula 3 are reacted with a suitable reducing agent, such as lithium aluminum hydride (LiAlH$_4$) to reduce the 2-oxo function and to provide N-alkylated or phenylated 6- or 7-amino 1,2,3,4-tetrahydroquinoline compounds of Formula 7. Thereafter, the amino compounds of Formula 7 are reacted with the reagent of Formula 4, as described above in connection with Reaction Scheme 1, to give the disubstituted amines of Formula 8 which are within the scope of the invention. The third substituent on the amino nitrogen is introduced by a reductive alkylation reaction that employs the aldehyde reagent R$_1$*—CHO, sodium cyamoborohydride and acetic acid usually in acetonitrile as the solvent. The group R$_1$*—is defined to the extent it can be made applicable, as the group R$_1$ in Formula 1 with one less CH$_2$ unit, that is a homolog having one CH$_2$ unit (carbon atom) less than the group $R_1$. The reductive alkylation reaction provides the trisubstituted amine compounds of Formula 9 within the scope of the invention, and which can be converted into further homologs and derivatives as described above in connection with Reaction Scheme 1.

Specific Embodiments

With reference to the symbol Y in Formula 1 the preferred compounds of the invention are those where Y is phenyl, naphthyl, pyridyl, thienyl or furyl. Even more preferred are compounds where Y is phenyl. As far as substitutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no $R_2$ substituent on the Y group.

The A—B group of the preferred compounds is $(CH_2)_q COOH$ or $(CH_2)_q$—$COOR_8$, where $R_8$ is defined as above. Even more preferably q is zero and $R_8$ is lower alkyl or the compound is a carboxylic acid, or a pharmaceutically acceptable salt thereof.

The $X_1$ and $X_2$ groups preferably jointly form an oxo (=O) group, or alternatively and preferably each of these two groups represents hydrogen.

$R_1$ is preferably an alkyl group, among the alkyl groups methyl, ethyl, branched-chain alkyl and cyclopropylmethyl groups are preferred. In this regard it should be noted that in the definition of this invention the term alkyl includes cycloalkyl and cycloalkylalkyl groups.

$R_2$ is preferably hydrogen or lower alkyl, more preferably hydrogen or methyl.

The $R_3$ substituents preferably are H or lower alkyl, even more preferably H or methyl. Still more preferably the symbol $(R_3)_0$ represents geminal dimethyl groups disposed in the 4-position of the tetrahydroquinoline nucleus.

The presently preferred $R_4$ groups are alkyl groups, more preferably branched chain alkyl, and still more preferably iso-propyl.

The most preferred compounds of the invention are disclosed in Table 2 with reference to Formulas 10 and 11.

Formula 10

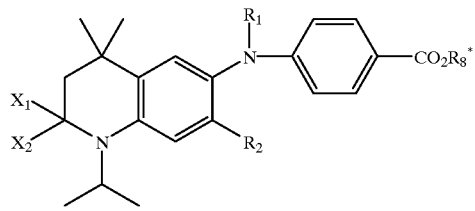

Formula 11

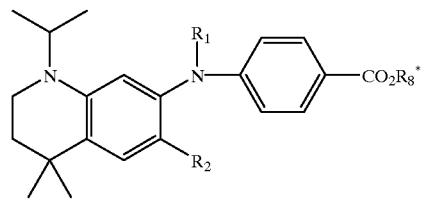

TABLE 2

| Compound No. | Formula | $X_1\ X_2$ | $R_2$ | $R_1$ | $R_8$* |
|---|---|---|---|---|---|
| 2 | 10 | $O^1$ | H | H | Et |
| 3 | 10 | $O^1$ | H | $CH_3$— | Et |
| 5 | 10 | $O^1$ | H | $CH_3$— | H |
| 4 | 10 | $O^1$ | H | $CH_3CH_2$— | Et |
| 6 | 10 | $O^1$ | H | $CH_3CH_2$— | H |
| 8 | 10 | H H | H | H | Et |
| 9 | 10 | H H | H | $CH_3$— | Et |
| 10 | 10 | H H | H | $CH_3$— | H |
| 11 | 10 | H H | H | $CH_3CH_2$— | Et |
| 12 | 10 | H H | H | $CH_3CH_2$— | H |
| 13 | 10 | H H | H | $(CH_3)_2CH(CH_2)_2$— | Et |
| 14 | 10 | H H | H | $(CH_3)_2CH(CH_2)_2$— | H |
| 20 | 10 | H H | $CH_3$ | H | Et |
| 23 | 10 | H H | $CH_3$ | $CH_3CH_2$— | Et |
| 24 | 10 | H H | $CH_3$ | $CH_3CH_2$— | H |
| 21 | 10 | H H | $CH_3$ | $CH_3$— | Et |
| 22 | 10 | H H | $CH_3$ | $CH_3$— | H |
| 25 | 10 | H H | $CH_3$ | cyclopropylmethyl | Et |
| 26 | 10 | H H | $CH_3$ | cyclopropylmethyl | H |
| 27 | 10 | H H | $CH_3$ | $(CH_3)_2CHCH_2$— | Et |
| 28 | 10 | H H | $CH_3$ | $(CH_3)_2CHCH_2$— | H |
| 34 | 11 | — | H | H | Et |
| 35 | 11 | — | H | $CH_3CH_2$— | Et |
| 38 | 11 | — | H | $CH_3CH_2$— | H |
| 36 | 11 | — | H | $(CH_3)_2CHCH_2$— | Et |
| 39 | 11 | — | H | $(CH_3)_2CHCH_2$— | H |
| 37 | 11 | — | H | cyclopropylmethyl | Et |
| 40 | 11 | — | H | cyclopropylmethyl | H |
| 46 | 11 | — | $CH_3$ | H | Et |
| 50 | 11 | — | $CH_3$ | H | H |
| 47 | 11 | — | $CH_3$ | $CH_3$ | Et |
| 51 | 11 | — | $CH_3$ | $CH_3$ | H |
| 48 | 11 | — | $CH_3$ | $CH_3CH_2$— | Et |
| 52 | 11 | — | $CH_3$ | $CH_3CH_2$— | H |
| 49 | 11 | — | $CH_3$ | $CH_3CH_2CH_2$— | Et |
| 53 | 11 | — | $CH_3$ | $CH_3CH_2CH_2$— | H |

Reaction Scheme 3 discloses the presently preferred synthesis of several exemplary compounds of the invention where the 2-position of the tetrahydroquinoline moiety includes an oxo function and the substituted amino group occupies the 6 position. A detailed description of the steps of this process is provided in the experimental section of this application for patent.

Reaction Schemes 4, 5, 6 and 7 disclose the presently preferred synthetic routes to compounds of the invention where the 2-position of the tetrahydroquinoline moiety is unsubstituted ($X_1$ and $X_2$ in Formula 1 are hydrogen) and where the substituted amino group occupies the 6 (Schemes 4 and 5) or 7 position (Schemes 6 and 7), respectively. Detailed description of the steps of these processes are also provided in the experimental section of this application for patent.

REACTION SCHEME 3

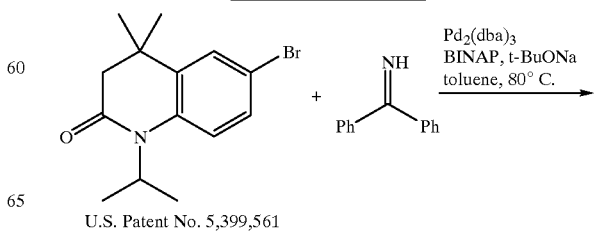

U.S. Patent No. 5,399,561

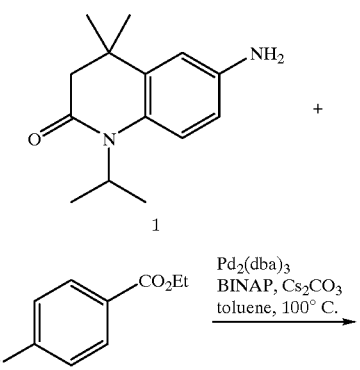
1
U.S. Patent No. 5,616,712
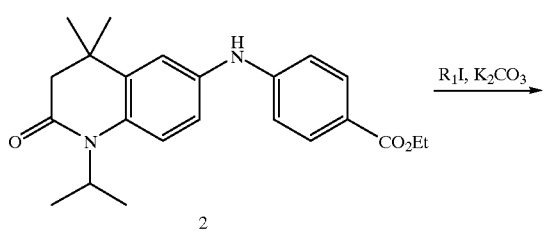
2
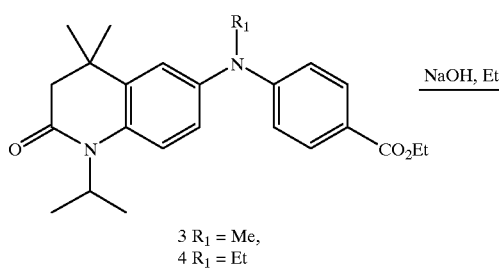
3 R₁ = Me,
4 R₁ = Et
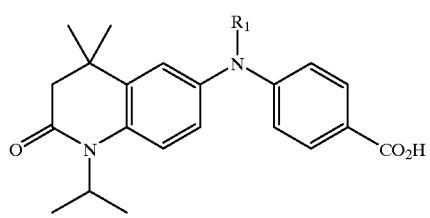
5 R₁ = Me
6 R₁ = Et
REACTION SCHEME 4
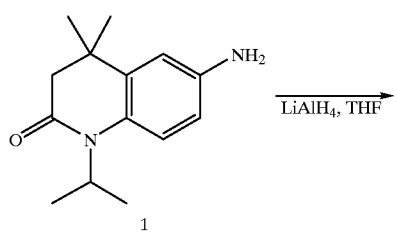
1
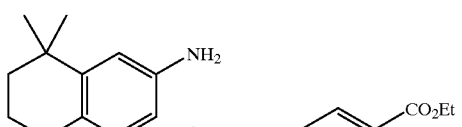
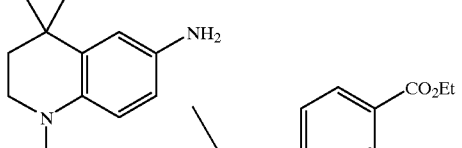
7
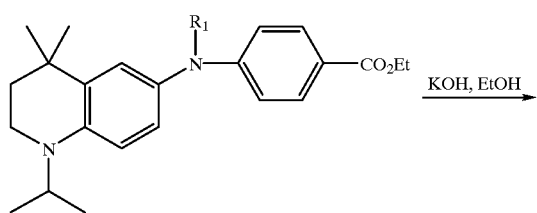
8
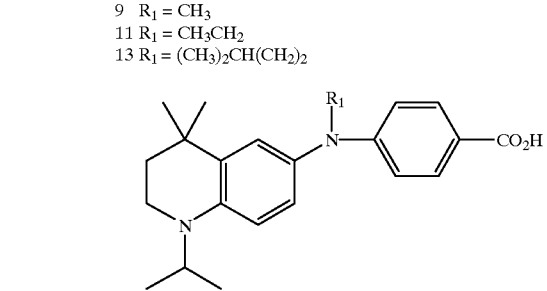
9  R₁ = CH₃
11 R₁ = CH₃CH₂
13 R₁ = (CH₃)₂CH(CH₂)₂
10 R₁ = CH₃
12 R₁ = CH₃CH₂
14 R₁ = (CH₃)₂CH(CH₂)₂

6,127,382
21  22
REACTION SCHEME 5
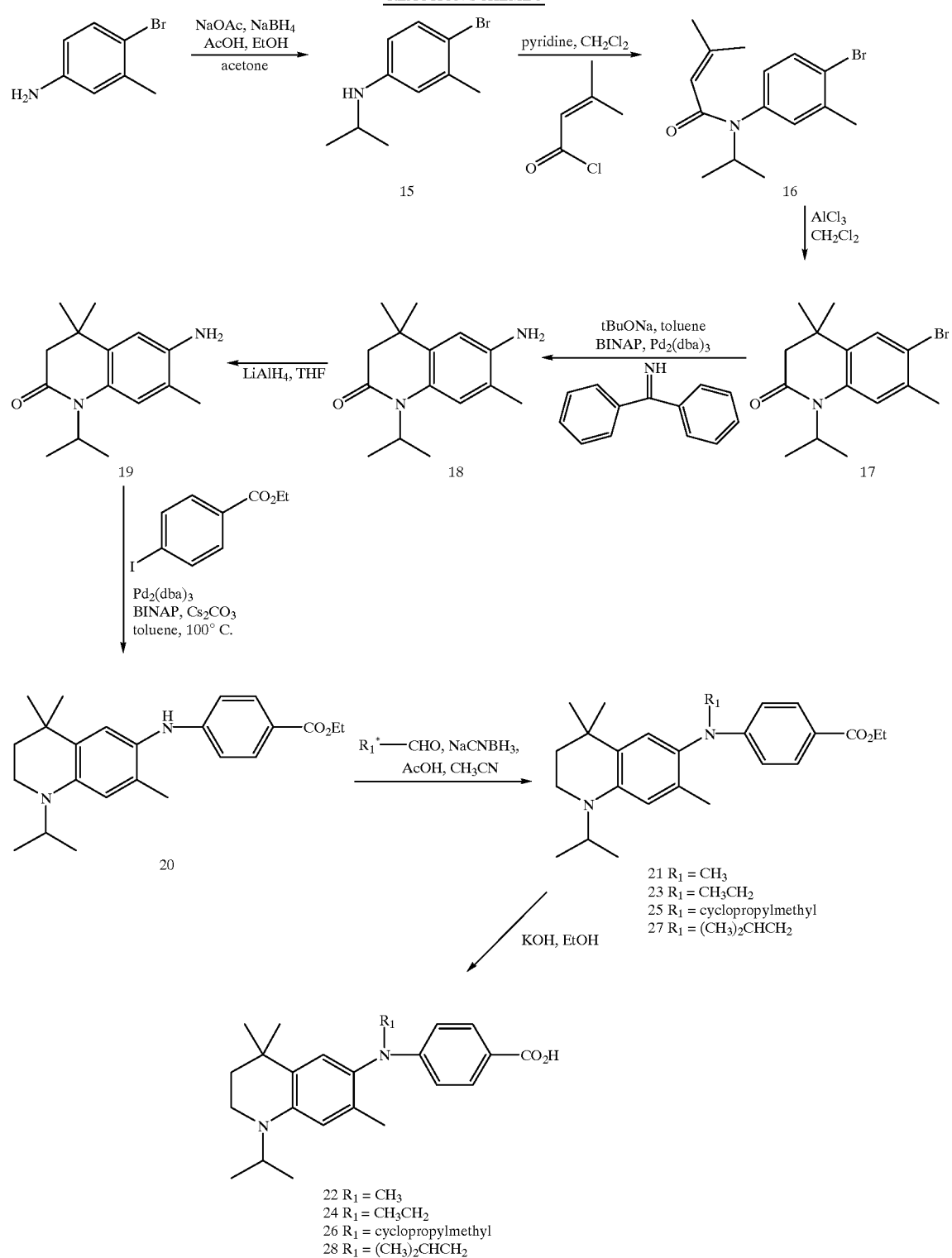

6,127,382
23
REACTION SCHEME 6
24
-continued
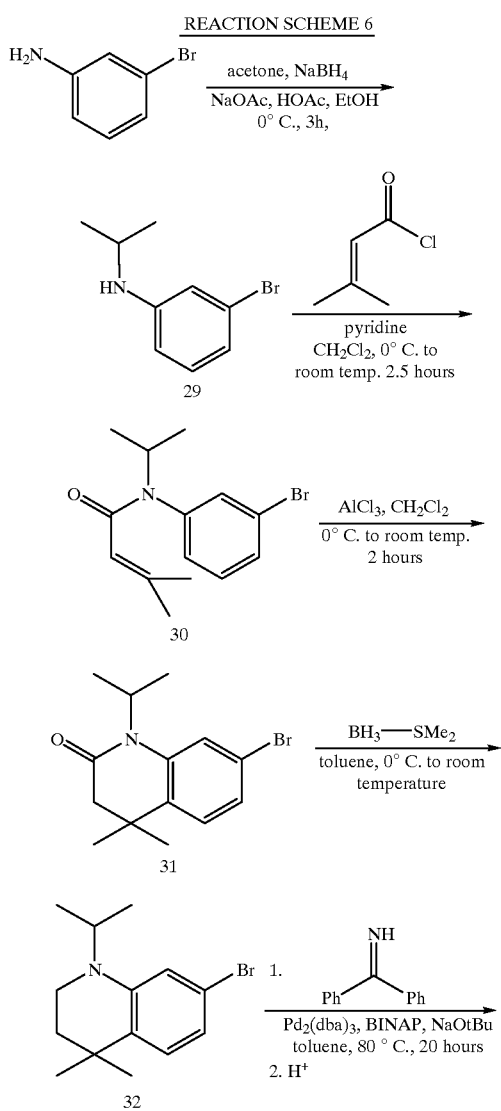
35 $R_1$ = ethyl
36 $R_1$ = $(CH_3)_2CHCH_2$
37 $R_1$ = cyclopropylmethyl
38 $R_1$ = ethyl
39 $R_1$ = $(CH_3)_2CHCH_2$
40 $R_1$ = cyclopropylmethyl
REACTION SCHEME 7

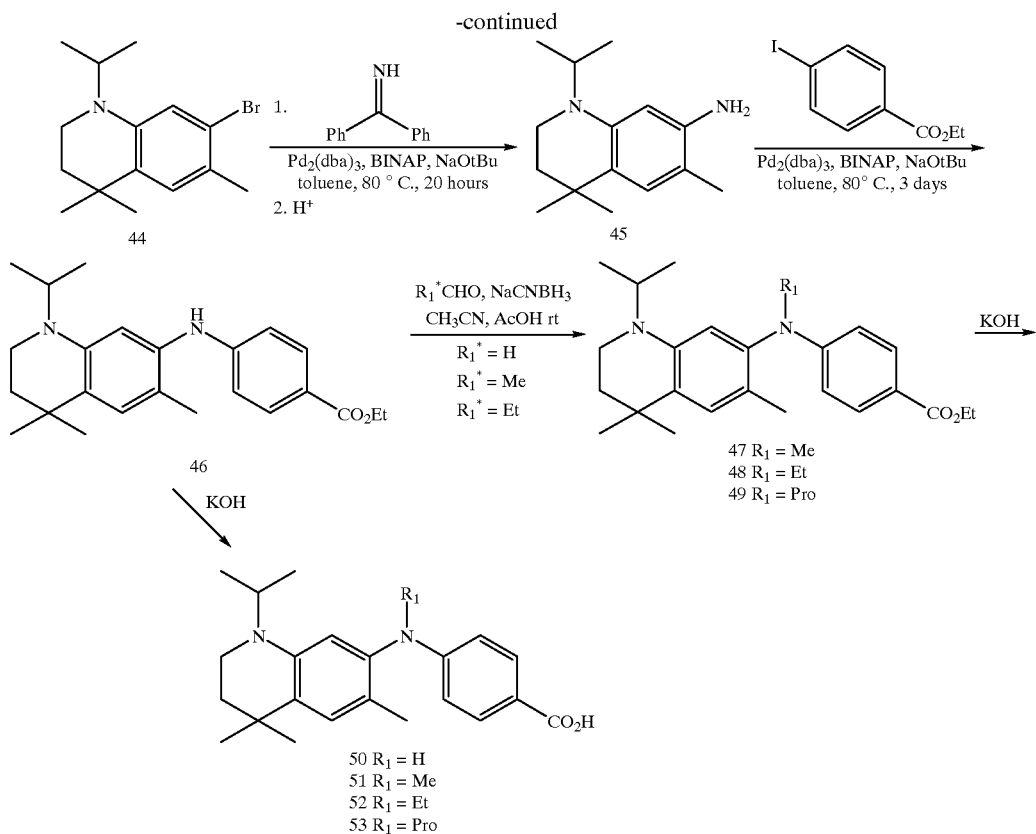

SPECIFIC EXAMPLES

(1-Isopropyl-4,4-dimethyl-2-oxo-1,2,3,4-tetrahydroquinolin-6-yl)amine (Compound 1)

A 25 mL round bottom flask was connected to a reflux condenser and the apparatus flame-dried under high vacuum. The vacuum was broken by the addition of dry argon, and the flask was allowed to cool to room temperature. The flask was charged with 0.135 g (1.4 mmol) of powdered sodium t-butoxide, 9.2 mg (0.01 mmol) of tris (dibenzylideneacetone)dipalladium(0) ($Pd_2(dba)_3$), and 19 mg (0.03 mmol) of (S)-(−)-2,2′-bis(diphenylphosphino)1,1′-binaphthyl (BINAP), and the apparatus was evacuated and filled with dry argon 3 times. A solution of 6-bromo-1-isopropyl-4,4-dimethyl-2-oxo-1,2,3,4-tetrahydroquinoline (0.296 mg, 1 mmol) available as described in U.S. Pat. No. 5,399,56, and benzophenone imine (0.218 g, 1.2 mmol) in 4 mL of dry toluene was added. The flask was immersed in an oil bath and heated to 80° C. until all of the starting material had been consumed as judged by thin layer chromatography (TLC) analysis. The solution was cooled to room temperature and diluted with 40 mL of ether. The mixture was filtered and concentrated in vacuo. The residue was dissolved in tetrahydrofuran (THF, 0.3 M) and 2.0 M HCl was added. The solution was stirred for 20 minutes at room temperature and partitioned between 0.5 M HCl and 2:1 hexane/ethyl acetate. The aqueous layer was made basic with 1 M NaOH and the product extracted with methylene chloride, dried over $Na_2SO_4$, and concentrated in vacuo. The residue was purified by flash chromatography on silica gel using 33% ethyl acetate in hexanes, to produce the title compound.

PNMR (300 MHz, $CDCl_3$) δ1.24 (s, 6H), 1.37 (d, 6H, J=6.9 Hz), 2.37 (s, 2 H), 3.61 (br s, 1 H), 4.68 (m, 1 H, J=6.9 Hz), 6.54 (dd, 1 H, J=2.7, 8.6 Hz), 6.63 (d, 1 H, J=2.7 Hz), 6.95 (d, 1 H, J=8.6 Hz).

Ethyl 4-[(1-isopropyl-4,4-dimethyl-2-oxo-1,2,3,4-tetrahydroquinolin-6-yl)amino]benzoate (Compound 2)

A 25 mL round bottom flask was connected to a reflux condenser and the apparatus flame-dried under high vacuum. The vacuum was broken by the addition of dry argon, and the flask was allowed to cool to room temperature. The flask was charged with 0.295 g (0.90 mmol) of powdered anhydrous cesium carbonate, 12 mg (0.013 mmol) of tris(dibenzylideneacetone)dipalladium(0) ($Pd_2(dba)_3$), and 12 mg (0.019 mmol) of (S)-(−)-2,2′-bis(diphenylphosphino)1,1′-binaphthyl (BINAP), and the apparatus was evacuated and filled with dry argon 3 times. A solution of (1-isopropyl-4,4-dimethyl-2-oxo-1,2,3,4-tetrahydroquinolin-6-yl)amine (Compound 1, 0.18 g, 775 mmol) and ethyl 4-iodoobenzoate (0.178 g, 0.65 mmol, available as described in U.S. Pat. No. 5,616,712) in 2 mL of dry toluene was added and the flask was immersed in an oil bath heated to 100° C. After 16 hours, 6 mg of $Pd_2(dba)_3$ and 6 mg of BINAP were added and stirring at 100° C. was continued until the reaction was complete as judged by TLC analysis. The solution was cooled to room temperature and poured into a separatory funnel containing water and ether. The layers were separated and the aqueous layer was extracted 3 times with ether. The combined ether layers were washed once with brine, and dried over magnesium sulfate, and the solvents were removed under reduced pressure. The residue was purified by flash chromatography on silica gel using 10% ethyl acetate in hexanes, and gave the title compound.

PNMR (300 MHz, CDCl$_3$) δ1.27 (s, 6 H), 1.38 (t, 3 H, J=7.1 Hz), 1.54 (d, 6 H, J=6.8 Hz), 2.43 (s, 2 H), 4.34 (q, 2 H, J=7.1 Hz), 4.71 (m, 1 H, J=6.8 Hz), 6.00 (s, 1 H), 6.93 (dd, 2 H, J=2.0, 6.8 Hz), 7.00–7.12 (several d's, 3 H), 7.90 (dd, 2 H, J=2.0, 6.8 Hz).

Ethyl 4-[(1-isopropyl-4,4-dimethyl-2-oxo-1,2,3,4-tetrahydroquinolin-6-yl)methylamino]benzoate (Compound 3)

General Procedure A: Methyl iodide (0.38 mL, 6.04 mmol) was added to a solution of ethyl 4-[(1-isopropyl-4,4-dimethyl-2-oxo-1,2,3,4-tetrahydroquinolin-6-yl)amino]benzoate (Compound 2, 0.115 g, 0.30 mmol) and 125 mg of potassium carbonate in 1 mL of dimethyl acetamide. The resealable tube was capped and the tube was immersed in an oil bath at 85° C. for 16 hours. The flask was cooled to room temperature, the seal broken, and the contents of the flask were transferred to a separatory funnel containing ether and water. The layers were separated and the aqueous layer was extracted 3 times with ether. The combined ether layers were washed once with brine, and dried over magnesium sulfate, and the solvents were removed under reduced pressure. The residue was purified by flash chromatography on silica gel using 1:5 ethyl acetate:hexane to give the title compound.

PNMR (300 MHz, CDCl$_3$) δ1.27 (s, 6 H), 1.36 (t, 3 H, J=7.1 Hz), 1.56 (d, 6 H, J=7.1 Hz), 2.44 (s, 2 H), 3.36 (s, 3 H), 4.34 (q, 2 H, J=7.2 Hz), 4.71 (m, 1 H, J=7.1 Hz), 6.73 (dd, 2 H, J=2.0, 7.1 Hz), 7.07 (dd, 1 H, J=2.4, 8.9 Hz), 7.12 (d, 1 H, J=2.4 Hz), 7.15 (d, 1 H, J=8.9 Hz), 7.87 (dd, 2 H, J=2.0, 7.1 Hz).

Ethyl 4-[(1-isopropyl-4,4-dimethyl-2-oxo-1,2,3,4-tetrahydroquinolin-6-yl)ethylamino]benzoate (Compound 4)

Using General Procedure A, ethyl 4-[(1-isopropyl-4,4-dimethyl-2-oxo-1,2,3,4-tetrahydroquinolin-6-yl)amino]benzoate (Compound 2, 0.115 g, 0.30 mmol) and ethyl iodide (0.48 mL, 6.0 mmol) were reacted to produce the title compound, which was purified by silica gel chromatography using 14% ethyl acetate in hexanes.

PNMR (300 MHz, CDCl$_3$) δ1.26 (t, 3 H, J=7.0 Hz), 1.27 (s, 6 H), 1.36 (t, 3 H, J=7.1 Hz), 1.57 (d, 6 H, J=7.0 Hz), 2.45 (s, 2H), 3.78 (q, 2 H, J=7.0 Hz), 4.32 (q, 2 H, J=7.1 Hz), 4.70 (m, 1 H, J=7.0 Hz), 6.66 (dd, 2 H, J=2.0, 8.9 Hz), 7.05 (dd, 1 H, J=2.6, 8.6 Hz), 7.09 (d, 1 H, J=2.6 Hz), 7.16 (d, 1 H, J=8.6 Hz), 7.85 (dd, 2 H, J=2.0, 8.9 Hz).

4-[(1-Isopropyl-4,4-dimethyl-2-oxo-1,2,3,4-tetrahydroquinolin-6-yl)methylamino]benzoic Acid (Compound 5)

General Procedure B: To a solution of ethyl 4-[(1-isopropyl-4,4-dimethyl-2-oxo-1,2,3,4-tetrahydroquinolin-6-yl)methylamino]benzoate, (Compound 3, 0.10 g, 0.25 mmol) and 4 mL of ethyl alcohol was added aqueous 1 N NaOH (1 mL). The resulting solution was heated in an 80° C. bath until the hydrolysis reaction was completed, as judged by thin layer chromatography. The solution was cooled to room temperature, diluted with water and washed once with 1:1 ether:hexane solution, and the layers were separated. The aqueous layer was acidified with 1 N aqueous HCl and the product extracted 3 times with ethyl acetate. The combined organic extracts were washed with brine, and dried over MgSO$_4$, and filtered, and the solvents were removed in vacuo to give the title compound as a light yellow solid.

PNMR (300 MHz, CDCl$_3$) δ1.28 (s, 6 H), 1.56 (d, 6 H, J=6.8 Hz), 2.46 (s, 2 H), 3.37 (s, 3 H), 4.71 (m, 1 H, J=6.8 Hz), 6.74 (d, 2 H, J=8.9 Hz), 7.07 (dd, 1 H, J=2.3, 8.4 Hz), 7.13 (d, 1 H, J=2.3 Hz), 7.17 (d, 1 H, J=8.4 Hz), 7.93 (d, 2 H, J=8.9 Hz).

4-[(1-Isopropyl-4,4-dimethyl-2-oxo-1,2,3,4-tetrahydroquinolin-6-yl)ethylamino]benzoic Acid (Compound 6)

Following General Procedure B, ethyl 4-[(1-isopropyl-4,4-dimethyl-2-oxo-1,2,3,4-tetrahydroquinolin-6-yl)ethylamino]benzoate (Compound 4, 0.07 g, 0.17 mmol) was hydrolyzed to give the title compound as a light yellow solid.

PNMR (300 MHz, CDCl$_3$) δ1.27 (t, 3 H, J=7.0 Hz), 1.27 (s, 6 H), 1.57 (d, 6 H, J=7.0 Hz), 2.47 (s, 2H), 3.79 (q, 2H, J=7.0 Hz), 4.70 (m, 1H, J=7.0 Hz), 6.67 (d, 2 H, J=9.0 Hz), 7.06 (dd, 1 H, J=2.4, 8.6 Hz), 7.11 (d, 1 H, J=2.4 Hz), 7.17 (d, 1 H, J=8.6 Hz), 7.91 (d, 2 H, J=9.0 Hz).

(1-Isopropyl-4,4-dimethyl-1,2,3,4-tetrahydroquinolin-6-yl)amine (Compound 7)

(1-Isopropyl-4,4-dimethyl-2-oxo-1,2,3,4-tetrahydroquinolin-6-yl)amine (Compound 1, 1.3 g, 5.6 mmol) was dissolved in tetrahydrofuran (80 mL) and the solution was cooled to 0° C. under argon. The solution was treated with 1M lithium aluminum hydride (15.0 mL, 15.0 mmol) and the reaction stirred at 0° C. to room temperature for 16 hours. The reaction was cooled to 0° C., poured onto ice and extracted with ether (2×). The combined organic extracts were washed with brine and dried (MgSO$_4$). The filtered solution was concentrated under reduced pressure and the crude product was purified by silica gel chromatography (5% ethyl acetate in hexanes) to give the title compound as an oil.

PNMR (300 MHz, CDCl$_3$): δ1.17 (d, 6 H, J=6.5 Hz), 1.22 (s, 6 H), 1.72 (t, 2 H, J=6.0 Hz), 3.07 (t, 2 H, J=6.0 Hz), 4.04 (p, 1 H, J=6.5 Hz), 6.51 (dd, 1 H, J=2.5, 8.8 Hz), 6.59 (d, 1 H, J=8.8 Hz), 6.68 (d, 1 H, J=2.5 Hz).

Ethyl 4-(1-isopropyl-4,4-dimethyl-1 2,3,4-tetrahydroquinolin-6-ylamino)benzoate (Compound 8)

To a solution of ethyl 4-bromobenzoate (0.95 g, 4.1 mmol) and (1-isopropyl-4-4-dimethyl-1,2,3,4-tetrahydroquinolin-6-yl)amine (Compound 7, 0.98 g, 4.5 mmol) in 8.0 mL of toluene stirring under argon was added cesium carbonate (2.08 g, 6.4 mmol), tris(dibenzylideneacetone)dipalladium(0) (42 mg, 0.05 mmol) and BINAP (40 mg, 0.06 mmol) consecutively. The reaction was then heated at 100° C. for 42 hours. During this time, additional tris(dibenzylideneacetone)dipalladium(0) (11 mg, 0.01 mmol) and BINAP (10 mg, 0.02 mmol) was added. The reaction was then cooled to room temperature, diluted with water and extracted with ethyl ether (2×). The combined organic extracts were washed with brine, and dried (MgSO$_4$). The filtered solution was concentrated under reduced pressure and the crude product was purified by silica gel chromatography (10% ethyl acetate in hexanes) to give the title compound (0.59 g, 39%) as an orange solid.

PNMR (300 MHz, CDCl$_3$): δ1.21 (d, 6 H, J=6.5 Hz), 1.26 (s, 6 H), 1.36 (t, 3 H, J=7.1 Hz) 1.71 (t, 2 H, J=6.1 Hz), 3.17 (t, 2 H, J=6.1 Hz), 4.11 (p, 1 H, J=6.5 Hz), 4.32 (q, 2 H, J=7.1 Hz), 5.75 (s, 1 H, NH), 6.68 (d, 1 H, J=8.8 Hz), 6.74 (d, 2 H, J=8.7 Hz), 6.91 (dd, 1 H, J=2.6, 8.8 Hz), 7.04 (d, 1 H, J=2.6 Hz), 7.86 (d, 2 H, J=8.7 Hz).

Ethyl 4-[(1-isopropyl-4,4-dimethyl-1,2,3,4-tetrahydroquinolin-6-yl)methylamino]-benzoate (Compound 9)

Ethyl 4-(1-isopropyl-4,4-dimethyl-1,2,3,4-tetrahydroquinolin-6-ylamino)benzoate (Compound 8, 44 mg, 0.12 mmol) was dissolved in a 10% acetic acid in acetonitrile solution (1.0 mL). The solution was treated with formaldehyde (0.05 mL, 1.80 mmol) and then sodium cyanoborohydride (11 mg, 0.17 mmol) and the reaction mixture was stirred at room temperature for 20 minutes. 1 M aqueous NaOH was added until pH=6 and the solution was extracted with ether (2×), washed with brine, and dried ($Na_2SO_4$). The filtered solution was concentrated under reduced pressure to give the title compound (43 mg, 94%) as an oil.

NMR (300 MHz, $CDCl_3$): δ1.22 (d, 6 H, J=6.6 Hz), 1.24 (s, 6 H), 1.35 (t, 3 H, J=7.0 Hz), 1.72 (t, 2 H, J=6.0 Hz), 3.19 (t, 2 H, J=6.0 Hz), 3.29 (s, 3 H), 4.12 (p, 1 H, J=6.6 Hz), 4.30 (q, 2 H, J=7.0 Hz), 6.63 (d, 2 H, J=9.0 Hz), 6.68 (d, 1 H, J=8.8 Hz), 6.86 (dd, 1 H, J=2.6, 8.8 Hz), 7.01 (d, 1 H, J=2.6 Hz), 7.83 (d, 2 H, J=9.0 Hz).

4-[(1-Isopropyl-4,4-dimethyl-1,2,3,4-tetrahydroquinolin-6-yl)methylamino]benzoic Acid (Compound 10)

Ethyl 4-[(1-isopropyl-4,4-dimethyl-1,2,3,4-tetrahydroquinolin-6-yl)methylamino]benzoate (Compound 9, 43 mg, 0.11 mmol) was dissolved in ethanol (4.0 mL) and the solution treated with 2.3 M KOH (1.0 mL). The solution was heated to 40° C. and stirred for 16 hours. The solution was cooled and concentrated under reduced pressure. The residue was diluted with water, acidified with 10% HCl, and extracted with ethyl acetate (2×). The combined organic layers were washed with brine, dried ($MgSO_4$), filtered and concentrated under reduced pressure. Purification by silica gel chromatography (30% ethyl acetate in hexanes) give the title compound (29 mg, 73%) as a solid.

PNMR (300 MHz, $d^6$ acetone): δ1.20 (d, 6 H, J=6.6 Hz), 1.24 (s, 6 H), 1.70 (t, 2 H, J=6.0 Hz), 3.22 (t, 2 H, J=6.0 Hz), 3.28 (s, 3 H), 4.18 (p, 1 H, J=6.6 Hz), 6.65 (d, 2 H, J=9.0 Hz), 6.77 (d, 1 H, J=8.9 Hz), 6.86 (dd, 1 H, J=2.6, 8.9 Hz), 7.05 (d, 1 H, J=2.6 Hz), 7.79 (d, 2 H, J=9.0 Hz).

Ethyl 4-[(1-isopropyl-4,4-dimethyl-1,2,3,4-tetrahydroquinolin-6-yl)ethylamino]benzoate (Compound 11)

Ethyl 4-[(1-isopropyl-4,4-dimethyl-1,2,3,4-tetrahydroquinolin-6-yl)amino]benzoate (Compound 8, 80 mg, 0.22 mmol) was dissolved in a 10% acetic acid in acetonitrile solution (2.0 mL). The solution was treated with acetaldehyde (0.10 mL, 1.80 mmol) and then sodium cyanoborohydride (18 mg, 0.29 mmol) and the reaction mixture was stirred at room temperature for 1.5 hours. 1M aqueous NaOH was added until pH=6 and the solution was extracted with ether (2×), washed with brine, and dried ($Na_2SO_4$). The filtered solution was concentrated under reduced pressure and the crude product was purified by silica gel chromatography (5% ethyl acetate in hexanes) to give the title compound (71 mg, 83%) as an oil.

PNMR (300 MHz, $CDCl_3$): δ1.20–1.24 (overlapping s, d, t, 15 H), 1.34 (t, 3 H, J=7.1 Hz), 1.72 (t, 2 H, J=6.0 Hz), 3.19 (t, 2 H, J=6.0 Hz), 3.70 (q, 2 H, J=7.0 Hz), 4.13 (p, 1 H, J=6.6 Hz), 4.30 (q, 2 H, J=7.1 Hz), 6.58 (d, 2 H, J=9.0 Hz), 6.69 (d, 1 H, J=8.8 Hz), 6.84 (dd, 1 H, J=2.6, 8.8 Hz), 6.97 (d, 1 H, J=2.6 Hz), 7.80 (d, 2 H, J=9.0 Hz).

4-[(1-Isopropyl-4,4-dimethyl-1,2,3,4-tetrahydroquinolin-6-yl)ethylamino]benzoic acid (Compound 12)

Ethyl 4-[(1-isopropyl-4,4-dimethyl-1,2,3,4-tetrahydroquinolin-6-yl)ethylamino]-benzoate (Compound 11, 71 mg, 0.18 mmol) was dissolved in ethanol (4.0 mL) and the solution treated with 2.3 M KOH (1.0 mL). The solution was heated to 40° C. and stirred for 18 hours. The solution was cooled and concentrated under reduced pressure. The residue was diluted with water, acidified with 10% HCl, and extracted with ethyl acetate (2×). The combined organic layers were washed with brine, dried ($MgSO_4$), filtered and concentrated under reduced pressure. Purification by recrystallization in ethanol gave the title compound (60 mg, 91%).

PNMR (300 MHz, $d^6$ acetone) δ1.20–1.24 (overlapping s, d, t, 15 H), 1.71 (t, 2 H, J=6.0 Hz),3.23 (t, 2 H, J=6.0 Hz), 3.71 (q, 2 H, J=7.1 Hz), 4.18 (p, 1 H, J=6.6 Hz), 6.61 (d, 2 H, J=9.1 Hz), 6.78 (d, 1H, J=8.8 Hz), 6.83 (dd, 1 H, J=2.5, 8.8 Hz), 7.01 (d, 1 H, J=2.5 Hz), 7.75 (d, 2 H, J=9.1 Hz).

Ethyl 4-[(1-isopropyl-4,4-dimethyl-1,2,3,4-tetrahydroquinolin-6-yl)(3-methylbutyl)amino] benzoate (Compound 13)

Ethyl 4-[(1-isopropyl-4,4-dimethyl-1,2,3,4-tetrahydroquinolin-6-yl)amino]benzoate (Compound 8, 37 mg, 0.10 mmol) was dissolved in a 10% acetic acid in acetonitrile solution (1.5 mL). The solution was treated with isovaleraldehyde (0.08 mL, 0.74 mmol) and then sodium cyanoborohydride (13 mg, 0.20 mmol) and the reaction mixture was stirred at room temperature for 5 hours. 1M aqueous NaOH was added until pH=6 and the solution was extracted with ether (2×), washed with brine, and dried ($Na_2SO_4$). The filtered solution was concentrated under reduced pressure and the residue purified by silica gel chromatography (5% ethyl acetate in hexanes) to give the title compound (20 mg, 45%) as an oil.

PNMR (300 MHz, $CDCl_3$) δ0.93 (d, 6 H, J=6.0 Hz), 1.23 (2s, 12 H), 1.34 (t, 3 H, J=7.1 Hz), 1.58 (m, 3 H), 1.72 (t, 2 H, J=6.0 Hz), 3.19 (t, 2 H, J=6.0 Hz), 3.63 (t, 2 H, J=8.1 Hz), 4.13 (p, 1 H, J=6.6 Hz), 4.30 (q, 2 H, J=7.1 Hz), 6.55 (d, 2 H, J=9.0 Hz), 6.68 (d, 1 H, J=9.0 Hz), 6.83 (dd, 1 H, J=2.5, 9.0 Hz), 6.97 (d, 1 H, J=2.5 Hz), 7.81 (d, 2 H, J=9.0 Hz).

4-[(1-Isopropyl-4,4-dimethyl-1,2,3,4-tetrahydroquinolin-6-yl)(3-methylbutyl)amino]-benzoic Acid (Compound 14)

Ethyl 4-[(1-isopropyl-4,4-dimethyl-1,2,3,4-tetrahydroquinolin-6-yl) (3-methylbutyl)amino]benzoate (Compound 13, 20 mg, 0.05 mmol) was dissolved in ethanol (4.0 mL) and the solution treated with 1.4 M KOH (1.0 mL). The solution was heated to 40° C. and stirred for 24 hours. The solution was cooled and concentrated under reduced pressure. The residue was diluted with water, acidified with 10% HCl, and extracted with ethyl acetate (2×). The combined organic layers were washed with brine, dried ($MgSO_4$), filtered and concentrated under reduced pressure to give the title compound (15 mg, 79%) as a solid.

PNMR (300 MHz, $d^6$ acetone): δ0.92 (d, 6 H, J=6.6 Hz), 1.22 (d, 6 H, J=6.6 Hz), 1.24 (s, 6 H), 1.53–1.66 (m, 3 H), 1.71 (t, 2 H, J=6.0 Hz), 3.22 (t, 2 H, J=6.0 Hz), 3.67 (t, 2 H, J=8.1 Hz), 4.18 (p, 1 H, J=6.6 Hz), 6.60 (d, 2 H, J=9.1 Hz), 6.78 (d, 1 H, J=9.0 Hz), 6.84 (dd, 1 H, J=2.5, 9.0 Hz), 7.02 (d, 1 H, J=2.5 Hz), 7.75 (d, 2 H, J=9.1 Hz).

(4-Bromo-3-methylphenyl)isopropylamine (Compound 15)

A solution of 4-bromo-3-methylaniline (5.05 g, 27 mmol) in acetic acid (6.0 mL), acetone (7.0 mL), ethanol (25.0 mL) and water (16.0 mL) was cooled to 0° C. and treated with sodium acetate (7.16 g, mmol). The reaction was stirred 5 minutes and then treated slowly and in several small portions with sodium borohydride (5.15 g, 136 mmol) and the resulting reaction mixture was stirred at 0° C. for 3 hours. The solution was neutralized with NaOH pellets and extracted with ether (2x). The combined organic extracts were washed with brine and dried (Na$_2$SO$_4$). The filtered solution was concentrated under reduced pressure to give the title compound (5.68 g, 92%) as an oil.

N-(4-Bromo-3-methylphenyl)-N-isopropyl(3-methylbut-2-en)amide (Compound 16)

To a solution of (4-bromo-3-methylphenyl) isopropylamine (Compound 15, 4.97 g, 22 mmol) in 50.0 mL of methylene chloride stirring under argon at 0° C. was added 3,3-dimethylacryloyl chloride (7.0 mL g, 88 mmol), and then pyridine (4.0 mL). The resulting reaction mixture was then stirred at 0° C. for 1 hour. The reaction mixture was then poured onto ice containing 10% HCl, and extracted with methylene chloride (2x). The combined organic extracts were washed with brine, and dried (MgSO$_4$). The filtered solution was partially concentrated under reduced pressure and the solution used in the next step without further isolation of the title compound.

PNMR (300 MHz, CDCl$_3$): δ1.05 (d, 6 H, J=7.0 Hz), 1.65 (s, 3 H), 2.10 (s, 3 H), 2.42 (s, 3 H), 5.00 (p, 1 H, J=7.0 Hz), 5.70 (s, 1 H), 6.76 (dd, 1 H, J=2.6, 8.4 Hz), 6.94 (d, 1 H, J=2.6 Hz), 7.54 (d, 1 H, J=8.4 Hz).

6-Bromo-1-isopropyl-4,4,7-trimethyl-2-oxo-1,2,3,4-tetrahydroquinoline (Compound 17)

To a suspension of aluminum chloride (15.5 g, 116 mmol) in methylene chloride (75 mL) stirring at 0° C. under argon, was added a solution of N-(4-bromo-3-methylphenyl)-N-isopropyl(3-methylbut-2-en)amide (Compound 16, 6.76 g, 22 mmol) in methylene chloride (25.0 mL) and the resulting mixture was stirred at 0° C. to room temperature for 18 hours. The reaction mixture was poured onto ice and extracted with methylene chloride (2x), washed with brine, and dried (Na$_2$SO$_4$). The filtered solution was concentrated under reduced pressure and the crude product was purified by silica gel chromatography (20% ethyl acetate in hexanes) to give the title compound (4.61 g, 68% 2 steps) as a solid.

PNMR (300 MHz, CDCl$_3$): δ1.27 (s, 6 H), 1.54 (d, 6 H, J=7.0 Hz), 1.76 (s, 3 H), 2.39 (s, 2 H), 4.65 (p, 1 H, J=7.0 Hz), 7.00 (s, 1 H), 7.39 (s, 1 H).

6-Amino-1-isopropyl-4,4,7-trimethyl-2-oxo-1,2,3,4-tetrahydroquinoline (Compound 18)

A solution of 6-bromo-1-isopropyl-4,4,7-trimethyl-2-oxo-1,2,3,4-tetrahydroquinoline (Compound 17, 2.86 g, 9.2 mmol), benzophenone imine (1.54 g, 8.5 mmol) in 25.0 mL of toluene was degassed with argon for 20 minutes. To this solution was added sodium t-butoxide (1.16 g, 1.2 mmol), tris(dibenzylideneacetone)dipalladium(0) (97 mg, 0.11 mmol) and BINAP (0.18 g, 0.29 mmol) consecutively. The reaction mixture was then heated at 80° C. for 24 hours. Thereafter it was cooled to room temperature, diluted with ether, filtered and concentrated. The residue was diluted with tetrahydrofuran (10.0 mL) and and 10% aqueous HCl and stirred for 1 hour. 0.5 M HCl and 30% hexane in ethyl acetate were then added. The layers were separated and the aqueous layer was made alkaline using saturated NaHCO$_3$ and water. The aqueous layer was extracted with methylene chloride (2x). The combined organic extracts were washed with brine and dried (Na$_2$SO$_4$). The filtered solution was concentrated under reduced pressure and the crude product was purified by silica gel chromatography (30% ethyl acetate in hexanes) to give the title compound (0.63 g, 56%) as a solid.

PNMR (300 MHz, CDCl$_3$): δ1.23 (s, 6 H), 1.51 (d, 6 H, J=7.0 Hz), 2.18 (s, 3 H), 2.35 (s, 2 H), 3.50 (broad s, 2 H, NH), 4.63 (p, 1 H, J=7.0 Hz), 6.60 (s, 1 H), 6.84 (s, 1 H).

(1-Isopropyl-4,4,7-trimethyl-1,2,3,4-tetrahydroquinolin-6-yl)amine (Compound 19)

6-Amino-1-isopropyl-4,4,7-trimethyl-2-oxo-1,2,3,4-tetrahydroquinoline (12) (0.78 g, 3.2 mmol) was dissolved in tetrahydrofuran (50 mL) and the solution was cooled to 0° C. under argon. The solution was treated with 1M lithium aluminum hydride (4.0 mL, 4.0 mmol) and the reaction stirred at 0° C. to room temperature for 24 hours. The reaction mixture was cooled to 0° C., poured onto ice and extracted with ether (2x). The combined organic extracts were washed with brine and dried (MgSO$_4$). The filtered solution was concentrated under reduced pressure and the crude product was purified by silica gel chromatography (5% ethyl acetate in hexanes) to give the title compound (0.87 g, >100%) as an oil.

PNMR (300 MHz, CDCl$_3$): δ1.16 (d, 6 H, J=7.0 Hz), 1.23 (s, 6 H), 1.68 (t, 2 H, J=6.0 Hz), 2.12 (s, 3 H), 3.05 (t, 2 H, J=6.0 Hz), 4.08 (p, 1 H, J=7.0 Hz), 6.59 (s, 1 H), 6.72 (s, 1 H).

Ethyl [(1-isopropyl-4,4,7-trimethyl-1,2,3,4-tetrahydroquinolin-6-yl)amino)benzoate (Compound 20)

To a solution of ethyl 4-bromobenzoate (0.98 g, 4.3 mmol) and (1-isopropyl-4,4,7-trimethyl-1,2,3,4-tetrahydroquinolin-6-yl)amine (Compound 19, 0.69 g, 3.0 mmol) in 15.0 mL of toluene stirring under argon was added cesium carbonate (1.84 g, 5.6 mmol), tris(dibenzylideneacetone)dipalladium(0) (35 mg, 0.04 mmol) and BINAP (68 mg, 0.11 mmol) consecutively. The reaction mixture was then heated at 100° C. for 48 hours. The reaction mixture was then cooled to room temperature, diluted with water and extracted with ethyl ether (2x). The combined organic extracts were washed with brine and dried (MgSO$_4$). The filtered solution was concentrated under reduced pressure and the crude product was purified by silica gel chromatography (10% ethyl acetate in hexanes) to give the title compound (0.63 g, 56% 2 steps) as an orange solid.

PNMR (300 MHz, CDCl$_3$): δ1.22 (d, 6 H, J=6.6 Hz), 1.24 (s, 6 H), 1.36 (t, 3 H, J=7.1 Hz) 1.71 (t, 2 H, J=6.0 Hz), 2.13 (s, 3 H), 3.18 (t, 2 H, J=6.0 Hz), 4.15 (p, 1 H, J=6.6 Hz), 4.32 (q, 2 H, J=7.1 Hz), 5.55 (s, 1 H, NH), 6.57 (d, 2 H, J=8.8 Hz), 6.58 (s, 1 H), 7.04 (s, 1H), 7.85 (d, 2 H, J=8.8 Hz).

Ethyl 4-[(1-isopropyl-4,4,7-trimethyl-1,2,3,4-tetrahydroquinolin-6-yl)methylamino]benzoate (Compound 21)

Ethyl [(1-isopropyl-4,4,7-trimethyl-1,2,3,4-tetrahydroquinolin-6-yl)amino)benzoate (Compound 20, 68 mg, 0.18 mol) was dissolved in a 10% acetic acid in acetonitrile solution (2.0 mL). The solution was treated with formaldehyde (0.10 mL, 3.60 mmol) and then with sodium cyanoborohydride (28 mg, 0.44 mmol) and the reaction mixture was stirred at room temperature for 2 hours. 1M aqueous NaOH was added until pH=6 was reached, and the solution was extracted with ether (2x), washed with brine, and dried (Na$_2$SO$_4$). The filtered solution was concentrated under reduced pressure and the residue purified using flash column chromatography (5% ethyl acetate in hexanes) to give the title compound (43 mg, 61%) as an oil.

PNMR (500 MHz, CDCl$_3$) δ1.19–1.21 (m, 12 H), 1.32 (t, 3 H, J=7.1 Hz) 1.67 (t, 2 H, J=6.0 Hz), 1.98 (s, 3H), 3.16 (t, 2 H, J=6.0 Hz), 3.21 (s, 3 H). 4.12 (p, 1 H, J=6.6 Hz), 4.28 (q, 2 H, J=7.1 Hz), 6.45 (d, 2 H, J=8.8 Hz), 6.53 (s, 1 H), 6.88 (s, 1 H), 7.81 (d, 2 H, J=8.8 Hz).

4-[(1-Isopropyl-4,4,7-trimethyl-1,2,3,4-tetrahydroquinolin-6-yl)methylamino]benzoic acid (Compound 22)

Ethyl 4-[(1-isopropyl-4,4,7-trimethyl-1,2,3,4-tetrahydroquinolin-6-yl)methylamino]benzoate (Compound 21, 43 mg, 0.11 mmol) was dissolved in ethanol (4.0 mL) and the solution treated with 1.8 M KOH (1.0 mL). The solution was heated to 40° C. and stirred for 24 hours. The solution was cooled and concentrated under reduced pressure. The residue was diluted with water, acidified with 10% HCl, and extracted with ether (2×). The combined organic layers were washed with brine, dried (MgSO$_4$), filtered and concentrated under reduced pressure. Purification by recrystallization in ethanol gave the title compound (25 mg, 63%).

PNMR (300 MHz, d$^6$ acetone): δ1.22 (d, 6 H, J=6.6 Hz), 1.23 (s, 6 H), 1.70 (t, 2 H, J=6.0 Hz), 1.99 (s, 3H), 3.22 (t, 2 H, J=6.0 Hz), 3.25 (s, 3 H), 4.22 (p, 1 H, J=6.6 Hz), 6.50 (d, 2 H, J=9.0 Hz), 6.68 (s, 1 H), 6.95 (s, 1 H), 7.80 (d,2 H, J=9.0 Hz).

Ethyl [(1-isopropyl-4,4,7-trimethyl-1,2,3,4-tetrahydroquinolin-6-yl)ethylamino]benzoate (Compound 23)

Ethyl [(1-isopropyl-4,4,7-trimethyl-1,2,3,4-tetrahydroquinolin-6-yl)amino)benzoate (Compound 20, 0.20 g, 0.53 mmol) was dissolved in a 10% acetic acid in acetonitrile solution (6.0 mL). The solution was treated with acetaldehyde (0.10 mL, 1.80 mmol) and then with sodium cyanoborohydride (64 mg, 1.0 mmol) and the reaction mixture was stirred at room temperature for 4 hours. 1M aqueous NaOH was added until pH=6 was reached and the solution was extracted with ether (2×), washed with brine, and dried (Na$_2$SO$_4$). The filtered solution was concentrated under reduced pressure and the residue purified using flash column chromatography (10% ethyl acetate in hexanes) to give the title compound (0.16 g, 76%) as an oil.

PNMR (300 MHz, CDCl$_3$): δ1.24 (overlapping s, d, t, 15 H), 1.35 (t, 3 H, J=7.1 Hz) 1.71 (t, 2 H, J=6.0 Hz), 2.01 (s, 3 H), 3.19 (t, 2 H, J=6.0 Hz), 3.49 (broad s, 1 H), 3.77 (broad s, 1 H), 4.16 (p, 1 H, J=7.0 Hz), 4.30 (q, 2 H, J=7.1 Hz), 6.46 (d, 2 H, J=9.0 Hz), 6.59 (s, 1 H), 6.88 (s, 1 H), 7.82 (d, 2 H, J=9.0 Hz).

4-[(1-Isopropyl-4,4,7-trimethyl-1,2,3,4-tetrahydroquinolin-6-yl)ethylamino]benzoic acid (Compound 24)

Ethyl [(1-isopropyl-4,4,7-trimethyl-1,2,3,4-tetrahydroquinolin-6-yl)ethylamino]benzoate (Compound 23, 0.16 g, 0.39 mmol) was dissolved in ethanol (4.0 mL) and the solution treated with 2.3 M KOH (1.0 mL). The solution was heated to 40° C. and stirred for 20 hours. The solution was cooled and concentrated under reduced pressure. The residue was diluted with water, acidified with 10% HCl, sat. ammonium chloride, and extracted with ether (2×). The combined organic layers were washed with brine, dried (MgSO$_4$), filtered and concentrated under reduced pressure. Purification by recrystallization in ethanol gave (115 mg, 77%) as light yellow crystals.

PNMR (300 MHz, d$^6$ acetone): δ1.20–1.24 (m, 15 H), 1.69 (t, 2 H, J 6.0 Hz), 1.98 (s, 3 H), 3.21 (t, 2 H, J=6.0 Hz), 3.50 (broad s, 1 H), 3.81 (broad s, 1 H), 4.21 (p, 1 H, J=6.6 Hz), 6.48 (d, 2 H, J=9.0 Hz), 6.69 (s, 1 H), 6.91 (s, 1 H), 7.77 (d, 2 H, J=9.0 Hz).

Ethyl [(1-isopropyl-4,4,7-trimethyl-1,2,3,4-tetrahydroquinolin-6-yl)(cyclopropylmethyl)amino] benzoate (Compound 25)

Ethyl [(1-isopropyl-4,4,7-trimethyl-1,2,3,4-tetrahydroquinolin-6-yl)amino)benzoate (Compound 20, 0.18 g, 0.47 mmol) was dissolved in a 10% acetic acid in acetonitrile solution (6.0 mL). The solution was treated with cyclopropylcarboxaldehyde (0.10 mL, 1.3 mmol) and then sodium cyanoborohydride (35 mg, 0.55 mmol) and the reaction was stirred at room temperature for 7 hours. 1M aqueous NaOH was added until pH=6 was reached and the solution was extracted with ether (2×), washed with brine, and dried (Na$_2$SO$_4$). The filtered solution was concentrated under reduced pressure and the residue purified using flash column chromatography (10% ethyl acetate in hexanes) to give the title compounds (0.1 g) as an oil.

PNMR (500 MHz, CDCl$_3$): δ0.16 (broad s, 2 H), 0.51 (broad s, 2 H), 1.19–1.23 (overlapping s&d, 12 H), 1.35 (t, 3 H, J=7.1 Hz) 1.71 (t, 2 H, J=6.0 Hz), 2.00 (s, 3 H), 3.08 (broad s, 1 H), 3.18 (t, 2 H, J=6.0 Hz), 3.79 (broad s, 1 H), 4.15 (p, 1 H, J=6.6 Hz), 4.30 (q, 2 H, J=7.1 Hz), 6.51 (d, 2 H, J=9.0 Hz), 6.57 (s, 1 H), 6.99 (s, 1 H), 7.83 (d, 2 H, J=9.0 Hz).

4-[(1-Isopropyl-4,4,7-trimethyl-1,2,3,4-tetrahydroquinolin-6-yl)(cyclopropylmethyl)amino]benzoic acid (Compound 26)

4 Ethyl [(1-isopropyl-4,4,7-trimethyl-1,2,3,4-tetrahydroquinolin-6-yl)(cyclopropylmethyl)amino] benzoate (Compound 25, 0.1 g, 0.2 mmol) was dissolved in ethanol (4.0 mL) and the solution treated with 1.7 M KOH (1.0 mL). The solution was heated to 40° C. and stirred for 24 hours. The solution was cooled and concentrated under reduced pressure. The residue was diluted with water, acidified with 10% HCl, and extracted with ether (2×). The combined organic layers were washed with brine, dried (MgSO$_4$), filtered and concentrated under reduced pressure. Purification by recrystallization in ethanol gave the title compound (63 mg, 67%).

PNMR (300 MHz, d$^6$acetone): δ0.16 (broad d, 2 H, J=4.5 Hz), 0.48 (broad d, 2 H, J=4.5 Hz), 1.17–1.28 (overlapping s&d, 12 H), 1.69 (t, 2 H, J=6.5 Hz), 1.98 (s, 3 H), 3.15 (broad s, 1 H), 3.21 (t, 2 H, J=6.6 Hz), 3.78 (broad s, 1 H), 4.20 (p, 1 H, J=6.6 Hz), 6.52 (d, 2 H, J=9.0 Hz), 6.67 (s, 1 H), 7.01 (s, 1 H), 7.78 (d, 2 H, J=9.0 Hz).

Ethyl [(1-isopropyl-4,4,7-trimethyl-1,2,3,4-tetrahydroquinolin-6-yl)isobutylamino]benzoate (Compound 27)

Ethyl [(1-isopropyl-4,4,7-trimethyl-1,2,3,4-tetrahydroquinolin-6-yl)amino)benzoate (Compound 20, 0.12 g, 0.32 mmol) was dissolved in a 10% acetic acid in acetonitrile solution (2.0 mL). The solution was treated with isobutyraldehyde (0.10 mL, 1.1 mmol) and then sodium cyanoborohydride (22 mg, 0.35 mmol) and the reaction stirred at room temperature for 7 hours. 1 M aqueous NaOH was added until pH=6 was reached and the solution was extracted with ether (2×), washed with brine, and dried (Na$_2$SO$_4$). The filtered solution was concentrated under reduced pressure and the residue purified using flash column chromatography (10% ethyl acetate in hexanes) to give the title compound (48 mg) as an oil.

PNMR (500 MHz, CDCl$_3$): δ0.98 (d, 6 H, J=6.6 Hz), 1.22 (overlapping s&d, 12 H), 1.33 (t, 3 H, J=7.1 Hz) 1.71 (t, 2 H, J=5.9 Hz), 1.95 (s, 3 H), 2.07 (p, 1 H, J=6.6 Hz), 3.16 (broad s, 1 H), 3.18 (t, 2 H, J=5.9 Hz), 3.62 (broad s, 1 H), 4.14 (p, 1 H, J=6.6 Hz), 4.28 (q, 2 H, J=7.1 Hz), 6.46 (d, 2 H, J=9.0 Hz), 6.56 (s, 1 H), 6.93 (s, 1 H), 7.79 (d, 2 H, J=9.0 Hz).

4-[(1-Isopropyl-4,4,7-trimethyl-1 2,3,4-tetrahydroquinolin-6-yl)isobutylamino]benzoic Acid (Compound 28)

Ethyl [(1-isopropyl-4,4,7-trimethyl-1,2,3,4-tetrahydroquinolin-6-yl)isobutylamino]benzoate (Compound 27, 48 mg, 0.11 mmol) was dissolved in ethanol (4.0 mL) and the solution treated with 1.5 M KOH (1.0 mL). The solution was heated to 40° C. and stirred for 24 hours. The solution was cooled and concentrated under reduced pressure. The residue was diluted with water, acidified with 10% HCl, and extracted with ether (2×). The combined organic layers were washed with brine, dried (MgSO$_4$), filtered and concentrated under reduced pressure. Purification by recrystallization in ethanol gave the title compound (15 mg, 33%) as ivory crystals.

PNMR (300 MHz, d$^6$ acetone) δ1.00 (d, 6 H, J=6.6 Hz), 1.22 (overlapping s&d, 12 H), 1.70 (t, 2 H, J=6.0 Hz), 1.96 (s, 3 H), 2.06 (m, 1 H), 2.83 (broad s, 1 H), 3.22 (t, 2 H, J=6.0 Hz), 3.70 (broad s, 1 H), 4.21 (p, 1 H, J=6.5 Hz), 6.51 (d, 2 H, J=9.1 Hz), 6.99 (s, 1 H), 7.75 (s, 1 H), 7.78 (d, 2 H, J=9.1 Hz).

(3-Bromophenyl)isopropylamine (Compound 29)

Sodium borohydride (16.5 g, 435 mmol) was added slowly over 2 hours to a mixture of 3-bromoaniline (10 g, 58.13 mmol), ethanol (58 mL), acetic acid (50 mL, 866.1 mmol), water (140 mL), acetone (35 mL, 482.5 mmol), and sodium acetate (15.8 g, 116.2 mmol). The solution was stirred at 0° C. for 3 hours. The reaction mixture was poured into 1:1 mixture of ether and hexane containing 2N KOH. The layers were separated and the aqueous layer was extracted with ether/hexane (1:1). The combined organic layers were washed once with water and brine, dried with MgSO$_4$, filtered, and concentrated under reduced pressure. The residue was purified by silica gel chromatography (10% ethyl acetate in hexane, Rf=0.31) to give the title compound (23.10 g, 93% as an oil:

PNMR (300 MHz, CDCl$_3$): δ1.21 (d, 6 H, J=6.5 Hz), 3.60 (m, 1 H), 6.48 (m, 1 H), 6.79–6.71 (m, 2 H), 7.01 (m, 1 H).

N-(3-Bromophenyl)-N-isopropyl(3-methylbut-2-en) amide (Compound 30)

(3-Bromophenyl)isopropylamine (Compound 29, 9.01 g, 42.08 mmol) was dissolved in dichloromethane (65 mL) and the solution was cooled to 0° C. and treated with 3,3-dimethylacryloyl chloride (7.48 g, 63.12 mmol). The solution was stirred at 0° C. for 1 hour and at room temperature for 1.5 hours. The mixture was poured into a separatory funnel containing dichloromethane and 10% aqueous HCl. The layers were separated and the aqueous layer extracted twice with dichloromethane. The combined organic layers were washed with water and brine, dried with MgSO$_4$, filtered, and concentrated under reduced pressure to give the title compound, which was used directly for the next reaction without further purification, as an oil: Rf=0.42, 20% ethyl acetate in hexane:

PNMR (300 MHz, CDCl$_3$): δ1.08 (d, 6 H, J=6.8 Hz), 1.65 (s, 3 H), 2.10 (s, 3 H), 5.00 (sp, 1 H, J=6.5 Hz), 5.24 (br s, 1 H), 7.03 (m, 1 H), 7.30–7.25 (m, 2 H), 7.51 (m, 1 H).

7-Bromo-1-isopropyl-4,4-dimethyl-2-oxo-1,2,3,4-tetrahydroquinoline (Compound 31)

N-(3-bromophenyl)-N-isopropyl(3-methylbut-2-en) amide (Compound 30, 12.46 g, 42.08 mmol) was dissolved in dichloromethane (400 mL) and the solution was cooled to 0° C. and treated with AlCl$_3$ (19.63 g, 147.28 mmol). The suspension was stirred at 0° C. for 1 hour and at room temperature for 1 hour and the reaction was quenched with ice. After 10% aqueous HCl was added, the layers were separated and the aqueous layer was extracted twice with dichloromethane. The combined organic layers were washed with water and brine, dried with MgSO$_4$, filtered, and concentrated under reduced pressure. The residue was filtered by silica gel chromatography (20% ethyl acetate in hexane, Rf=0.48) to give the title compound as an oil:

PNMR (300 MHz, CDCl$_3$): δ1.27 (s, 6 H), 1.54 (d, 6 H, J=7.0 Hz), 2.40 (s, 2 H), 4.62 (m, 1 H), 7.27–7.11 (m, 3 H).

7-Bromo-1-isopropyl-4,4-dimethyl-1,2,3,4-tetrahydroquinoline (Compound 32)

7-Bromo-1-isopropyl-4,4-dimethyl-2-oxo-1,2,3,4-tetrahydroquinoline (Compound 31, 12.46 g, 42.08 mmol) was dissolved in toluene (100 mL) and the solution was cooled to 0° C. and treated with 2.0 M of BH$_3$.SMe$_2$ (23.14 mL, 46.28 mmol) in THF. The solution was stirred at 0° C. for 1 hour and at room temperature overnight, and the reaction mixture was treated with 10% aqueous Na$_2$CO$_3$. The solution was stirred at room temperature for 1 hour, the layers were separated and the aqueous layer extracted twice with ethyl acetate. The combined organic layers were washed with water and brine, dried with MgSO$_4$, filtered, and concentrated under reduced pressure. The residue was purified by silica gel chromatography (2% ethyl acetate in hexane, Rf=0.31) to give the title compounds (11.28 g, 95% over 3 steps) as an oil:

PNMR (300 MHz, CDCl$_3$): δ1.22 (d, 6 H, J=6.6 Hz), 1.26 (s, 6 H), 1.68 (t, 2 H, J=6.1 Hz), 3.19 (t, 2 H, J=6.1 Hz), 4.07 (sp, 1 H, J=6.6 Hz), 6.71 (dd, 1 H, J=8.2, 1.9 Hz), 6.80 (d, 1 H, J=2.2 Hz), 7.04 (m, 1 H).

7-Amino-1-isopropyl-4,4-dimethyl-1,2,3,4-tetrahydroquinoline (Compound 33)

A mixture of 7-bromo-1-isopropyl-4,4-dimethyl-1,2,3,4-tetrahydroquinoline (Compound 32, 1.24 g, 4.393 mmol), Pd$_2$(dab)$_3$ (20.10 mg, 0.25 mol %), BINAP (41.04 mg, 0.75 mol %), benzophenone imine (1.147 g, 5.27 mmol), and NaOtBu (591 mg, 6.15 mmol) in toluene (15 mL) was stirred at 80° C. for 20 hours. The reaction mixture was cooled to room temperature, diluted with ether, filtered through Celite, and concentrated under reduced pressure to give crude intermediate imine. The imine was dissolved in THF (13 mL) and treated with 2 M HCl (0.65 mL). After 30 minutes, the reaction mixtures were partitioned between 0.5 M HCl and ethyl acetate/hexane (1:2). The aqueous layer was separated and made alkaline and the product was extracted with dichloromethane. The combined organic layers were dried with MgSO$_4$, filtered, and concentrated under reduced pressure. The residue was purified by silica gel chromatography (10% ethyl acetate in hexane, Rf=0.10) to give the title compound (805.7 mg, 84%) as a solid:

PNMR (300 MHz, CDCl$_3$): δ1.21 (d, 6 H, J=6.6 Hz), 1.25 (s, 6 H), 1.68 (t, 2 H, J=6.0 Hz), 3.16 (t, 2 H, J=6.0 Hz), 3.47 (brs, 2 H), 4.08 (sp, 1 H, J=6.6 Hz), 6.02 (dd, 1 H, J=8.2, 2.2 Hz), 6.09 (s, 1 H), 7.00 (d, 1 H, J=7.9 Hz).

Ethyl 4-[(1-isopropyl-4,4-dimethyl-1,2,3,4-tetrahydroquinolin-7-yl)amino]benzoate (Compound 34)

7-Amino-1-isopropyl-4,4-dimethyl-1,2,3,4-tetrahydroquinoline (Compound 33, 130 mg, 0.5954 mmol) was placed into the round bottom flask charged with argon and Pd$_2$(dab)$_3$ (1.363 mg, 0.25 mol %), and BINAP (2.78 mg, 0.75 mol %) were added, followed by addition of NaOtBu (80.11 mg, 0.8335 mmol), ethyl iodobenzoate (230 mg, 0.8335 mmol) and toluene (3 mL). The resulting mixture was stirred at 80° C. for 3 days, cooled to room temperature, and filtered through Celite. The filtrate was concentrated under reduced pressure and the residue was purified by silica gel chromatography (10% ethyl acetate in hexane, Rf=0.30) to give the title compound (90.3 mg, 41%) as a solid: PNMR (300 MHz, CDCl$_3$): δ1.20 (d, 6 H, J=6.6 Hz), 1.28 (s, 6 H), 1.38 (t, 3 H, J=7.1 Hz), 1.71 (t, 2 H, J=6.0 Hz), 3.19 (t, 2 H, J=6.0 Hz), 4.02 (sp, 1 H, J=6.6 Hz), 4.34 (q, 2 H, J=7.1 Hz), 5.92 (s, 1 H), 6.43 (dd, 1 H, J=8.1, 2.1 Hz), 6.50 (d, 1 H, J=2.1 Hz), 6.97 (d, 2 H, J=8.7 Hz), 7.14 (d, 1 H, J=8.1 Hz), 7.90 (d, 2 H, J=8.7 Hz).

Ethyl 4-[(1-isopropyl-4,4-dimethyl-1,2,3,4-tetrahydro-quinolin-7-yl)ethylamino]-benzoate (Compound 35)

A solution of ethyl 4-[(1-isopropyl-4,4-dimethyl-1,2,3,4-tetrahydroquinolin-7-yl)amino]benzoate (Compound 34, 8 mg, 0.0218 mmol), acetaldehyde (4.8 mg, 0.1091 mmol), sodium cyanoborohydride (6.86 mg, 0.1091 mmol), acetic acid (0.125 mL), and acetonitrile (1 mL) was stirred at room temperature overnight. The solvent was removed and the residue was purified by silica gel chromatography (10% ethyl acetate in hexane, Rf=0.41) to give the title compound (5.6 mg, 65%) as a solid:

PNMR (300 MHz, CDCl$_3$): δ1.16 (d, 6 H, J=6.5 Hz), 1.25 (t, 3 H, J=7.1 Hz), 1.30 (s, 6 H), 1.35 (t, 3 H, J=7.1 Hz), 1.73 (t, 2 H, J=6.1 Hz), 3.18 (t, 2 H, J=6.1 Hz), 3.78 (q, 2 H, J=7.1 Hz), 3.98 (sp, 1 H, J=6.6 Hz), 4.31 (q, 2 H, J=7.1 Hz), 6.40 (dd, 1 H, J=7.9, 2.0 Hz), 6.49 (d, 1 H, J=1.7 Hz), 6.67 (dd, 2 H, J=9.1, 2.1 Hz), 7.19 (d, 1 H, J=8.0 Hz), 7.82 (dd, 2 H, J=9.0, 2.1 Hz).

4-[(1-isopropyl-4,4-dimethyl-1,2,3,4-tetrahydroquinolin-7-yl)isobutylamino]benzoate (Compound 36)

A solution of 4-[(1-isopropyl-4,4-dimethyl-1,2,3,4-tetrahydroquinolin-7-yl)amino]benzoate (Compound 34, 9.5 mg, 0.0259 mmol), isobutyraldehyde (9.34 mg, 0.1296 mmol), sodium cyanoborohydride (8.14 mg, 0.1296 mmol), acetic acid (0.125 mL), and acetonitrile (1 mL) was stirred at room temperature for 3 days. The solvent was removed and the residue was purified by silica gel chromatography (10% ethyl acetate in hexane, Rf=0.49) to give the title compound (6.2 mg, 57%) as a solid:

PNMR (300 MHz, CDCl$_3$): δ0.97 (d, 6 H, J=6.6 Hz), 1.16 (d, 6 H, J=6.6 Hz), 1.29 (s, 6 H), 1.35 (t, 3 H, J=7.1 Hz), 1.73 (t, 2 H, J=6.0 Hz), 2.09 (sp, 1 H, J=6.7 Hz), 3.17 (t, 2 H, J=6.0 Hz), 3.51 (d, 2 H, J=7.4 Hz), 3.96 (sp, 1 H, J=6.6 Hz), 4.31 (q, 2 H, J=7.1 Hz), 6.41 (dd, 1 H, J=8.1, 2.0 Hz), 6.50 (d, 1 H, J=2.0 Hz), 6.69 (d, 2 H, J=9.0 Hz), 7.17 (d, 1 H, J=8.1 Hz), 7.81 (d,2 H, J=9.0 Hz).

Ethyl 4-[(1-isopropyl-4,4-dimethyl-1,2,3,4-tetrahydro-quinolin-7-yl)(cyclopropylmethyl)amino]benzoate (Compound 37)

A solution of 4-[(1-isopropyl-4,4-dimethyl-1,2,3,4-tetrahydroquinolin-7-yl)amino]benzoate (Compound 34, 9.4 mg, 0.0256 mmol), cyclopropylcarboxaldehyde (8.99 mg, 0.1282 mmol), sodium cyanoborohydride (8.06 mg, 0.1282 mmol), acetic acid (0.125 mL), and acetonitrile (1 mL) was stirred at room temperature for 3 days. The solvent was removed and the residue was purified by silica gel chromatography (10% ethyl acetate in hexane, Rf=0.48) to give the title compound (8.03 mg, 75%) as a solid: PNMR (300 MHz, CDCl$_3$): δ0.19 (m, 2 H), 0.49 (m, 2 H), 1.16 (d, 6 H, J=6.5 Hz), 1.30 (s, 6 H), 1.35 (t, 3 H, J=7.1 Hz), 1.73 (t, 2 H, J=6.0 Hz), 3.17 (t, 2 H, J=6.0 Hz), 3.56 (d, 2 H, J=6.5 Hz), 3.99 (sp, 1 H, J=6.6 Hz), 4.31 (q, 2 H, J=7.1 Hz), 6.43 (dd, 1 H, J=8.1, 2.0 Hz), 6.53 (d, 1 H, J=3.6 Hz), 7.71 (d, 2 H, J=9.0 Hz), 7.18 (d, 1 H, J=8.0 Hz), 7.83 (d, 2 H, J=9.0 Hz).

4-[(1-Isopropyl-4,4-dimethyl-1,2,3,4-tetrahydroquinolin-7-yl)ethylamino]benzoic acid (Compound 38)

A solution ethyl 4-[(1-isopropyl-4,4-dimethyl-1,2,3,4-tetrahydroquinolin-7-yl)ethylamino]-benzoate (Compound 35, 5.6 mg, 0.0142 mmol) of 7 in ethanol (1 mL) was treated with 2N KOH (0.5 mL) and stirred at 50° C. for 2 days. The solvent was removed under reduced pressure and the residue was washed with ethyl acetate and acidified with 2N HCl. The aqueous layer was extracted with ethyl acetate and the combined organic layers were dried with MgSO$_4$, filtered, and concentrated under reduced pressure. The residue was purified by silica gel chromatography (20% ethyl acetate in hexane, Rf=0.11) to give the title compound (5.2 mg, quant.) as a pale yellow solid:

PNMR (500 MHz, CDCl$_3$): δ1.21 (d, 6 H, J=6.6 Hz), 1.28 (t, 3 H, J=7.0 Hz), 1.33 (s, 6 H), 1.78 (t, 2 H, J=6.0 Hz), 3.24 (t, 2 H, J=6.0 Hz), 3.80 (q, 2 H, J=7.0 Hz), 4.01 (sp, 1 H, J=6.6 Hz), 6.49 (d, 1 H, J=8.1 Hz), 6.58 (s 1 H), 6.70 (d, 2 H, J=8.9 Hz), 7.24 (d, 1 H, J=8.1 Hz), 7.90 (d, 2 H, J=8.9 Hz): $^{13}$C NMR (125 MHz, CDCl$_3$): δ172.15, 152.63, 145.55, 144.14, 131.81, 130.31, 127.23, 115.97, 114.06, 112.25, 110.17, 47.05, 46.68, 37.04, 36.47, 31.96, 30.54, 18.62, 12.50.

4-[(1-Isopropyl-4,4-dimethyl-1 2,3,4-tetrahydroquinolin-7-yl)isobutylamino]benzoic acid (Compound 39)

A solution of 4-[(1-isopropyl-4,4-dimethyl-1,2,3,4-tetrahydroquinolin-7-yl)isobutylamino]benzoate (Compound 36, 6.2 mg, 0.01467 mmol) in ethanol (1 mL) was treated with 2N KOH (0.5 mL) and stirred at 50° C. for 2 days. The solvent was removed under reduced pressure and the residue was washed with ethyl acetate and acidified with 2N HCl. The aqueous layer was extracted with ethyl acetate and the combined organic layers were dried with MgSO$_4$, filtered, and concentrated under reduced pressure. The residue was purified by silica gel chromatography (20% ethyl acetate in hexane, Rf=0.11) to give the title compound (5.4 mg, 93%) as a pale yellow solid:

PNMR (500 MHz, CDCl$_3$): δ1.00 (d, 6 H, J=6.6 Hz), 1.19 (d, 6 H, J=6.6 Hz), 1.32 (s, 6 H), 1.76 (t, 2 H, J=6.0 Hz), 2.12

(sp, 1 H, J=6.8 Hz), 3.20 (t, 2 H, J=6.0 Hz), 3.55 (d, 2 H, J=7.3 Hz), 3.99 (sp, 1 H, J=6.6 Hz), 6.44 (d, 1 H, J=8.1 Hz), 6.52 (s, 1 H), 6.72 (d, 2 H, J=9.2 Hz), 7.21 (d, 1 H, J=8.1 Hz), 7.89 (d, 2 H, J=9.2 Hz): $^{13}$C NMR (125 MHz, CDCl$_3$): δ172.11, 153.85, 145.48, 145.02, 131.61, 130.04, 127.14, 116.35, 113.91, 113.07, 110.07, 59.92, 47.07, 37.10, 36.49, 31.93, 30.59, 27.23, 20.44, 18.59.

4-[(1-Isolpropyl-4,4-dimethyl-1,2,3,4-tetrahydroquinolin-7-yl)(cylopropylmethyl)amino] benzoic acid (Compound 40)

A solution of ethyl 4-[(1-isopropyl-4,4-dimethyl-1,2,3,4-tetrahydroquinolin-7-yl)(cyclopropylmethyl)amino] benzoate (Compound 37, 8.03 mg, 0.0191 mmol) in ethanol (1 mL) was treated with 2N KOH (0.5 mL) and stirred at 50° C. for 2 days. The solvent was removed under reduced pressure and the residue was washed with ethyl acetate and acidified with 2N HCl. The aqueous layer was extracted with ethyl acetate and the combined organic layers were dried with MgSO$_4$, filtered, and concentrated under reduced pressure. The residue was purified by silica gel chromatography (20% ethyl acetate in hexane, Rf=0.11) to give the title compound (7.5 mg, quant.) as a pale yellow solid:

PNMR (500 MHz, CDCl$_3$): δ0.22(m, 2 H), 0.54 (m, 2 H), 1.19 (d, 6 H, J=6.4 Hz), 1.32 (s, 6 H), 1.76 (t, 2 H, J=5.3 Hz), 3.20 (t, 2 H, J=5.3 Hz), 3.59 (d, 2 H, J=6.6 Hz), 4.02 (sp, 1 H, J=6.6 Hz), 6.46 (d, 1 H, J=7.8 Hz), 6.57 (s, 1 H), 6.74 (dd, 2 H, J=9.0, 1.7 Hz), 7.22 (d, 1 H, J=7.8 Hz), 7.91 (dd, 2 H, J=9.0, 1.7 Hz): $^{13}$C NMR (125 MHz, CDCl$_3$): δ172.21, 153.18, 144.77, 131.79, 127.17, 116.12, 114.38, 112.39, 110.54, 56.55, 47.06, 37.09, 36.49, 31.97, 30.61, 29.71, 18.64, 9.64, 3.96.

(3-Bromo-4-methyl-phenyl)-isopropyl-amine (Compound 41)

Sodium borohydride (30.5 g, 806.2 mmol) was added slowly over 3 hours to a stirring mixture of 3-bromo-4-methylaniline (30 g, 161.2 mmol), ethanol (110 mL), acetic acid (92 mL, 1.6 mol), water (265 mL), acetone (66 mL, 892.2 mmol), and sodium acetate (29.2 g, 214.9 mmol). The solution was stirred at 0° C. for 1 hour. The reaction mixture was poured into the 1:1 mixture of ether and hexane containing 2N KOH. The layers were separated and aqueous layer was extracted with ether/hexane (1:1). The combined organic layers were washed once with water and brine, dried with MgSO$_4$, filtered, and concentrated under reduced pressure. The residue was used directly for the next reaction without further purification:

$^1$H NMR (300 MHz, CDCl$_3$): δ1.20 (d, 6 H, J=6.2 Hz), 2.28 (s, 3 H), 3.58 (sp, 1 H, J=6.2 Hz), 6.46 (dd, 1 H, J=8.2, 2.4 Hz), 6.80 (d, 1 H, J=2.4 Hz), 7.01 (d, 1 H, J=8.2 Hz).

3-Methyl-but-2-enoic acid (3-bromo-4-methyl-phenyl)-isopropyl-amide (Compound 42)

(3-Bromo-4-methyl-phenyl)-isopropyl-amine (Compound 41, 36.78 g, 161.2 mmol) was dissolved in dichloromethane (200 mL) and the solution was cooled to 0° C. and treated with 3,3-dimethylacryloyl chloride (28.6 g, 241.8 mmol) and then pyridine (36 mL). The solution was stirred at 0° C. for 1 hour and at room temperature for 5 hours. The mixture was poured into separatory funnel containing dichloromethane and 10% aqueous HCl. The layers were separated and the aqueous layer extracted twice with dichloromethane. The combined organic layers were washed with water and brine, dried with MgSO$_4$, filtered, and concentrated under reduced pressure to give the title compound, which was used directly for the next reaction without further purification, as a solid: Rf=0.48, 20% ethyl acetate in hexane:

$^1$H NMR (300 MHz, CDCl$_3$): δ1.06 (d, 6 H, J=6.8 Hz), 1.65 (s, 3 H), 2.10 (s, 3 H), 2.44 (s, 3 H), 5.00 (sp, 1 H, J=6.4 Hz), 5.26 (s, 1 H), 6.92 (dd, 1 H, J=8.0, 2.0 Hz), 7.23–7.26 (m, 2 H).

7-Bromo-1-isopropyl-4,4,6-trimethyl-3 4-dihydro-1H-quinolin-2-one (Compound 43)

3-Methyl-but-2-enoic acid (3-bromo-4-methyl-phenyl)-isopropyl-amide (Compound 42, 50 g, 161.2 mmol) was dissolved in dichloromethane (800 mL) and the solution was cooled to 0° C. and treated with AlCl$_3$ (75.23 g, 564.2 mmol). The suspension was stirred at 0° C. for 1 hour and at room temperature for 1 hour and the reaction was quenched with ice. After 10% aqueous HCl was added, the layers were separated and the aqueous layer extracted twice with dichloromethane. The combined organic layers were washed with water and brine, dried with MgSO$_4$, filtered, and concentrated under reduced pressure. The residue was filtered by silica gel chromatography (10% ethyl acetate in hexane, Rf=0.38) to give the title compound as an oil:

$^1$H NMR (300 MHz, CDCl$_3$): δ1.25 (s, 6 H), 1.52 (d, 6 H, J=6.9 Hz), 2.36 (s, 3 H), 2.38 (s, 2 H), 4.62 (sp, 1 H, J=7.0 Hz), 7.10 (s, 1 H), 7.27 (s, 1 H).

7-Bromo-1-isopropyl-4,4,6-trimethyl-1,2,3,4-tetrahydro-quinoline (Compound 44)

7-Bromo-1-isopropyl-4,4,6-trimethyl-3,4-dihydro-1H-quinolin-2-one (Compound 43, 50 g, 161.2 mmol) was dissolved in toluene (300 mL) and the solution was cooled to 0° C. and treated with 2.0 M of BH$_3$.SMe$_2$ (20 mL, 193.44 mmol) in THF. The solution was stirred at 0° C. for 1 hour and at room temperature over night, and at 60° C. for 1 day. Thereafter the reaction mixture was treated with 10% aqueous Na$_2$CO$_3$. The solution was stirred at room temperature for 1 hour, the layers were separated and the aqueous layer extracted twice with ethyl acetate. The combined organic layers were washed with water and brine, dried with MgSO$_4$, filtered, and concentrated under reduced pressure. The residue was purified by silica gel chromatography (2% ethyl acetate in hexane, Rf=0.35) to give the title compound (37.8 g, 79% over 4 steps) as an oil:

$^1$H NMR (300 MHz, CDCl$_3$): δ1.52 (d, 6 H, J=6.6 Hz), 1.60 (s, 6 H), 1.97 (t, 2 H, J=6.0 Hz), 2.66 (s, 3 H), 3.44 (t, 2 H, J=6.0 Hz), 4.35 (sp, 1 H, J=6.6 Hz), 7.24 (s, 1 H), 7.37 (s, 1 H).

1-Isopropyl-4,4,6-trimethyl-1,2,3,4-tetrahydro-quinolin-7-ylamine (Compound 45)

A mixture of 7-bromo-1-isopropyl-4,4,6-trimethyl-1,2,3, 4-tetrahydroquinoline (Compound 44, 5 g, 21.53 mmol), Pd$_2$(dab)$_3$ (96.56 mg, 0.5 mol %), BINAP (201 mg, 1.5 mol %), benzophenone imine (5.46 g, 30.14 mmol), and NaOtBu (2.896 g, 30.14 mmol) in toluene (40 mL) was stirred at 80° C. for 20 hours. The reaction mixture was cooled to room temperature, diluted with ether, filtered through Celite, and concentrated under reduced pressure to give crude intermediate imine derivative. The imine was dissolved in THF (52 mL) and treated with 2 M HCl (2.6 mL). After 30 minutes, the reaction mixtures were partitioned between 0.5 M HCl and ethyl acetate/hexane (1:2). The aqueous layer was separated and made alkaline and the product was extracted with dichloromethane. The combined organic layers were dried with MgSO₄, filtered, and concentrated under reduced pressure. The residue was purified by silica gel chromatography (20% ethyl acetate in hexane, Rf=0.21) to give the title compound (2.3 g, 46%):

¹H NMR (300 MHz, CDCl₃): δ1.22 (d, 6 H, J=6.6 Hz), 1.29 (s, 6 H), 1.71 (t, 2 H, J=6.0 Hz), 2.13 (s, 3 H), 3.15 (t, 2 H, J=6.0 Hz), 3.46 (s, 2 H), 4.09 (sp, 1 H, J=6.6 Hz), 6.15 (s, 1 H), 6.90 (s, 1 H).

4-(1-Isopropyl-4,4,6-trimethyl-1,2,3,4-tetrahydro-quinolin-7-ylamino)-benzoic acid ethyl ester (Compound 46)

1-Isopropyl-4,4,6-trimethyl-1,2,3,4-tetrahydro-quinolin-7-ylamine (Compound 45, 500 mg, 2.152 mmol) was placed into the round bottom flask charged with argon. Pd₂(dab)₃ (4.926 mg, 0.25 mol %), and BINAP (10.05 mg, 0.75 mol %) were added, followed by NaOtBu (405.27 mg, 3.012 mmol), ethyl iodobenzoate (831.7 mg, 3.012 mmol) and toluene (8 mL). The resulting mixture was stirred at 80° C. for 3 days, cooled to room temperature, and filtered through Celite. The filtrate was concentrated under reduced pressure and the residue was purified by silica gel chromatography (10% ethyl acetate in hexane, Rf=0.26) to give the title compound (642.76 mg, 79%) as a pale yellow solid:

¹H NMR (300 MHz, CDCl₃): δ1.16 (d, 6 H, J=6.6 Hz), 1.29 (s, 6 H), 1.37 (t, 3 H, J=7.1 Hz), 1.72 (t, 2 H, J=6.0 Hz), 2.11 (s, 3 H), 3.15 (t, 2 H, J=6.0 Hz), 3.97 (sp, 1 H, J=6.6 Hz), 4.33 (q, 2 H, J=7.1 Hz), 5.64 (s, 1 H), 6.62 (s 1 H), 6.79 (dd, 2 H, J=8.9, 2.4 Hz), 7.04 (s, 1 H), 7.89 (dd, 2 H, J=8.9, 2.4 Hz)

4-[(1-Isopropyl-4,4,6-trimethyl-1,2,3,4-tetrahydro-quinolin-7-yl)-methyl-amino]-benzoic acid ethyl ester (Compound 47)

A solution of 4-(1-isopropyl-4,4,6-trimethyl-1,2,3,4-tetrahydroquinolin-7-ylamino)-benzoic acid ethyl ester (Compound 46, 30 mg, 0.0788 mmol), formaldehyde (23.66 mg, 0.788 mmol), sodium cyanoborohydride (3.9 mg, 0.788 mmol), acetic acid (0.125 mL), and acetonitrile (1 mL) was stirred at room temperature overnight. The solvent was removed and the residue was purified by silica gel chromatography (5% ethyl acetate in hexane, Rf=0.27) to give the title compound(9.5 mg, 31%) as a white solid:

¹H NMR (300 MHz, CDCl₃): δ1.15 (d, 6 H, J=6.6 Hz), 1.30 (s, 6 H), 1.35 (t, 3 H, J=7.1 Hz), 1.73 (t, 2 H, J=6.0 Hz), 1.96 (s, 3 H), 3.14 (t, 2 H, J=6.0 Hz), 3.26 (s, 3 H), 3.97 (sp, 1 H, J=6.6 Hz), 4.31 (q, 2 H, J=7.1 Hz), 6.51 (d, 2 H, J=8.9 Hz), 7.06 (s, 1 H), 7.85 (d, 2 H, J=8.9 Hz).

4-[Ethyl-(1-isopropyl-4,4,6-trimethyl-1,2,3,4-tetrahydro-quinolin-7-yl)-ethylamino]-benzoic acid ethyl ester (Compound 48)

A solution of 4-(1-isopropyl-4,4,6-trimethyl-1,2,3,4-tetrahydroquinolin-7-ylamino)-benzoic acid ethyl ester (Compound 46, 64.4 mg, 0.1692 mmol), acetaldehyde (37.2 mg, 0.8462 mmol), sodium cyanoborohydride (53.2 mg, 0.8462 mmol), acetic acid (0.125 mL), and acetonitrile (1 mL) was stirred at room temperature overnight. The solvent was removed and the residue was purified by silica gel chromatography (10% ethyl acetate in hexane, Rf=0.44) to give the title compound (71.2 mg, 52%) as a solid: ¹H NMR (300 MHz, CDCl₃): δ1.15 (d, 6 H, J=6.5 Hz), 1.27 (t, 3 H, J=7.1 Hz), 1.31 (s, 6 H), 1.35 (t, 3 H, J=7.1 Hz), 1.74 (t, 2 H, J=6.0 Hz), 1.96 (s, 3 H), 3.15 (t, 2 H, J=6.0 Hz), 3.68 (d, 2 H, J=5.9), 3.98 (sp, 1 H, J=6.5 Hz), 4.31 (q, 2 H, J=7.1 Hz), 6.43 (s, 1 H), 6.49 (d, 2 H, J=8.9 Hz), 7.08 (s, 1 H), 7.84 (d, 2 H, J=8.9 Hz).

4-[(1-Isopropyl-4,4,6-trimethyl-1,2,3,4-tetrahydro-quinolin-7-yl)-propyl-amino]-benzoic acid ethyl ester (Compound 49)

A solution of 4-(1-isopropyl-4,4,6-trimethyl-1,2,3,4-tetrahydroquinolin-7-ylamino)-benzoic acid ethyl ester (Compound 46, 60.3 mg, 0.1585 mmol), propionaldehyde (36.4 mg, 0.792 mmol), sodium cyanoborohydride (49.77 mg, 0.792 mmol), acetic acid (0.125 mL), and acetonitrile (1 mL) was stirred at room temperature overnight. The solvent was removed and the residue was purified by silica gel chromatography (10% ethyl acetate in hexane, Rf=0.44) to give the title compound (12.0 mg, 18%) as a solid:

¹H NMR (300 MHz, CDCl₃): δ0.94 (t, 3 H, J=7.3 Hz), 1.15 (d, 6 H, J=6.6 Hz), 1.30 (s, 6 H), 1.34 (t, 3 H, J=7.1 Hz), 1.68–1.78 (m, 4 H), 1.94 (s, 3 H), 3.14 (t, 2 H, J=5.9 Hz), 3.53 (br s, 2 H), 3.97 (sp, 1 H, J=6.6 Hz), 4.30 (q, 2 H, J=7.1 Hz), 6.42–6.47 (m, 3 H), 7.07 (s, 1 H), 7.82 (d, 2 H, J=8.4 Hz).

4-(1-Isopropyl-4,4,6-trimethyl-1,2,3,4-tetrahydro-quinolin-7-ylamino)-benzoic acid (Compound 50)

A solution of 4-(1-isopropyl-4,4,6-trimethyl-1,2,3,4-tetrahydroquinolin-7-ylamino)-benzoic acid ethyl ester (Compound 46, 10.5 mg, 0.0275 mmol) in ethanol (1 mL) was treated with 2N KOH (0.5 mL) and stirred at 50° C. for 18 hours. The solvent was removed under reduced pressure and the residue was washed with ethyl acetate and acidified with 2N HCl. The aqueous layer was extracted with ethyl acetate and the combined organic layers were dried with MgSO₄, filtered, and concentrated under reduced pressure. The residue was purified by silica gel chromatography (30% ethyl acetate in hexane, Rf=0.10) to give the title compound (9.3 mg, 96%) as a white solid: ¹H NMR (300 MHz, CDCl₃): δ1.17 (d, 6 H, J=6.6 Hz), 1.29 (s, 6 H), 1.72 (t, 2 H, J=6.0 Hz), 2.12 (s, 3 H), 3.15 (t, 2 H, J=6.0 Hz), 3.98 (sp, 1 H, J=6.6 Hz), 5.72 (br s, 1 H), 6.62 (s, 1 H), 6.79 (d, 2 H, J=8.7 Hz), 7.05 (s, 1 H), 7.96 (d, 2 H, J=8.7 Hz)

4-[(1-Isopropyl-4,4,6-trimethyl-1,2,3,4-tetrahydro-quinolin-7-yl)-methyl-amino]-benzoic acid (Compound 51)

A solution of 4-[(1-isopropyl-4,4,6-trimethyl-1,2,3,4-tetrahydroquinolin-7-yl)-methyl-amino]-benzoic acid ethyl ester (Compound 47, 8.9 mg, 0.02256 mmol) in ethanol (1 mL) was treated with 2N KOH (0.5 mL) and stirred at 50° C. for 18 hours. The solvent was removed under reduced pressure and the residue was washed with ethyl acetate and acidified with 2N HCl. The aqueous layer was extracted with ethyl acetate and the combined organic layers were dried with MgSO₄, filtered, and concentrated under reduced pressure. The residue was purified by silica gel chromatography (50% ethyl acetate in hexane, Rf=0.22) to give the title compound (7 mg, 85%) as a white solid:

¹H NMR (300 MHz, CDCl₃): δ1.15 (d, 6 H, J=6.6 Hz), 1.30 (s, 6 H), 1.73 (t, 2 H, J=6.0 Hz), 1.96 (s, 3 H), 3.15 (t, 2 H, J=6.0 Hz), 3.28 (s, 3 H), 3.97 (sp, 1 H, J=6.6 Hz), 6.44 (s, 1 H), 6.52 (d, 2 H, J=8.7 Hz), 7.07 (s, 1 H), 7.90 (d, 2 H, J=8.7 Hz).

4-[-(1-Isopropyl-4,4,6-trimethyl-1,2,3,4-tetrahydro-quinolin-7-yl)ethylamino]-benzoic acid (Compound 52)

A solution of 4-Ethyl-(1-isopropyl-4,4,6-trimethyl-1,2,3,4-tetrahydroquinolin-7-yl)-ethylamino]-benzoate (Compound 48, 65 mg, 0.1591 mmol) in ethanol (1 mL) was treated with 2N KOH (0.5 mL) and stirred at 50° C. for 2 days. The solvent was removed under reduced pressure and the residue was washed with ethyl acetate and acidified with 2N HCl. The aqueous layer was extracted with ethyl acetate and the combined organic layers were dried with $MgSO_4$, filtered, and concentrated under reduced pressure. The residue was purified by silica gel chromatography (40% ethyl acetate in hexane, Rf=0.22) to give the title compound (63.2 mg, quant) as a white solid:

$^1$H NMR (300 MHz, $CDCl_3$): δ1.16 (d, 6 H, J=6.6 Hz), 1.28 (t, 3 H, J=3.6 Hz), 1.32 (s, 6 H), 1.75 (t, 2 H, J=6.0 Hz), 1.98 (s, 3 H), 3.15 (t, 2 H, J=6.0 Hz), 3.69 (br s, 2 H), 3.99 (sp, 1 H, J=6.6 Hz), 6.43 (s, 1 H), 6.51 (d, 2 H, J=8.8 Hz), 7.09 (s, 1 H), 7.90 (d, 2 H, J=8.8 Hz).

4-[(1-Isopropyl-4,4,6-trimethyl-1,2,3,4-tetrahydro-quinolin-7-yl)-propyl-amino]-benzoic acid (Compound 53)

A solution 4-[(1-isopropyl-4,4,6-trimethyl-1,2,3,4-tetrahydro-quinolin-7-yl)-propyl-amino]-benzoic acid ethyl ester (Compound 49, 12.0 mg, 0.0284 mmol) in ethanol (1 mL) was treated with 2N KOH (0.5 mL) and stirred at 50° C. for 2 days. The solvent was removed under reduced pressure and the residue was washed with ethyl acetate and acidified with 2N HCl. The aqueous layer was extracted with ethyl acetate and the combined organic layers were dried with $MgSO_4$, filtered, and concentrated under reduced pressure. The residue was purified by silica gel chromatography (30% ethyl acetate in hexane, Rf=0.28) to give the title compound (11 mg, 98%) as a white solid: $^1$H NMR (300 MHz, $CDCl_3$): δ0.95 (t, 3 H, J=7.4 Hz), 1.16 (d, 6 H, J=6.6 Hz), 1.31 (s, 6 H), 1.69–1.80 (m, 4 H), 1.95 (s, 3 H), 3.15 (t, 2 H, J=5.9 Hz), 3.54 (br s, 2 H), 3.97 (sp, 1 H, J=6.6 Hz), 6.47 (d, 2 H, J=8.9 Hz), 7.08 (s, 1 H), 7.88 (d, 2 H, J=8.9 Hz).

What is claimed is:

1. A compound of the formula

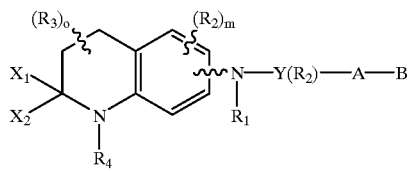

wherein $X_1$ and $X_2$ independently are H, or alkyl of 1 to 6 carbons, or F, or the $X_1$ and $X_2$ groups jointly symbolize an oxo (=O) or thio (=S) function;

$R_1$ is H, alkyl of 1 to 10 carbons, cycloalkylalkyl of 4 to 10 carbons, phenyl-$C_1$–$C_6$ alkyl, $C_1$–$C_6$-alkylphenyl, heteroaryl-$C_1$–$C_6$ alkyl, or $C_1$–$C_6$-alkylheteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

$R_2$ is independently H, alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer having the values of 0 to 3;

$R_3$ is independently H, alkyl of 1 to 6 carbons, or F;

o is in an integer having the values of 0 to 4;

$R_4$ is H, alkyl of 1 to 10 carbons, phenyl, phenyl-$C_1$–$C_6$-alkyl, naphthyl, naphthyl-$C_1$–$C_6$-alkyl, or heteroaryl selected from a group consisting of pyridyl, thienyl, furyl, pyridazinyl, pyrimidinyl, pyrazinyl, thiazolyl, oxazolyl, imidazolyl and pyrrazolyl, or heteroaryl-$C_1$–$C_6$-alkyl, said phenyl, naphthyl and heteroaryl groups being optionally substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, or $COOR_1$;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

2. A compound in accordance with claim 1 wherein Y is a bivalent phenyl, naphthyl, thienyl, furyl or pyridyl group.

3. A compound in accordance with claim 1 wherein $X_1$ and $X_2$ jointly represent an oxo group.

4. A compound in accordance with claim 1 wherein $X_1$ and $X_2$ each is hydrogen.

5. A compound in accordance with claim 1 wherein the $R_4$ group is alkyl.

6. A compound in accordance with claim 5 wherein the $R_4$ group is branch-chained alkyl.

7. A compound in accordance with claim 1 wherein the A—B group represents $(CH_2)_q$—COOH, $(CH_2)_q$—$COOR_8$ or a pharmaceutically acceptable salt thereof.

8. A compound in accordance with claim 1 wherein the $R_1$ is H or alkyl of 1 to 10 carbons, or cycloalkylalkyl having 4 to 10 carbons.

9. A compound in accordance with claim 1 wherein the amino function is attached to the 6 position of the tetrahydroquinoline ring.

10. A compound in accordance with claim 1 wherein the amino function is attached to the 7 position of the tetrahydroquinoline ring.

11. A compound of the formula

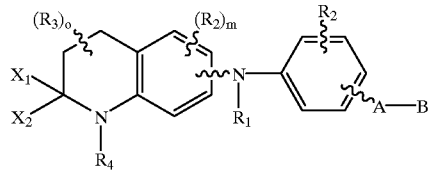

wherein $X_1$ and $X_2$ independently are H, or alkyl of 1 to 6 carbons, or the $X_1$ and $X_2$ groups jointly symbolize an oxo (=O) function;

$R_1$ is H, alkyl of 1 to 10 carbons, or cycloalkylalkyl of 4 to 10 carbons;

$R_2$ is independently H, alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer having the values of 0 to 3;

$R_3$ is independently H, alkyl of 1 to 6 carbons, or F;

o is in an integer having the values of 0 to 4;

$R_4$ is H, alkyl of 1 to 10 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound, and wherein the amino moiety is attached to the 6 or 7 position of the tetrahydroquinoline ring.

12. A compound in accordance with claim 11 wherein $X_1$ and $X_2$ jointly represent an oxo group.

13. A compound in accordance with claim 12 wherein $(R_3)_o$ represents a geminal dimethyl group in the 4 position of the tetrahydroquinoline ring.

14. A compound in accordance with claim 13 wherein $R_2$ is hydrogen or lower alkyl.

15. A compound in accordance with claim 14 wherein the A—B group represents $(CH_2)_q$—COOH, $(CH_2)_q$—$COOR_8$ where q is 0, or a pharmaceutically acceptable salt of said compound.

16. A compound in accordance with claim 11 wherein $X_1$ and $X_2$ each is hydrogen.

17. A compound in accordance with claim 16 wherein $(R_3)_o$ represents a geminal dimethyl group in the 4 position of the tetrahydroquinoline ring.

18. A compound in accordance with claim 17 wherein $R_2$ is hydrogen or lower alkyl.

19. A compound in accordance with claim 18 wherein the A—B group represents $(CH_2)_q$—COOH, $(CH_2)_q$—$COOR_8$ where q is 0, or a pharmaceutically acceptable salt of said compound.

20. A compound of the formula

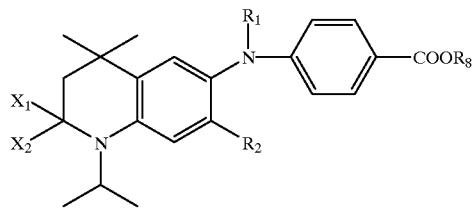

wherein $X_1$ and $X_2$ each are H, or the $X_1$ and $X_2$ groups jointly symbolize an oxo (=O) function;

$R_1$ is H, alkyl of 1 to 10 carbons, or cycloalkylalkyl of 4 to 10 carbons;

$R_2$ is H or methyl, and $R_8$ is H, lower alkyl, or a pharmaceutically acceptable salt of said compound.

21. A compound in accordance with claim 20 wherein the $X_1$ and $X_2$ groups jointly symbolize an oxo (=O) function.

22. A compound in accordance with claim 21 wherein $R_1$ is hydrogen.

23. A compound in accordance with claim 21 wherein $R_1$ is methyl.

24. A compound in accordance with claim 21 wherein $R_1$ is ethyl.

25. A compound in accordance with claim 20 wherein $X_1$ and $X_2$ each is hydrogen.

26. A compound in accordance with claim 25 wherein $R_1$ is hydrogen.

27. A compound in accordance with claim 25 wherein $R_1$ is methyl.

28. A compound in accordance with claim 25 wherein $R_1$ is ethyl.

29. A compound in accordance with claim 25 wherein $R_1$ is the radical $(CH_3)_2CH(CH_2)_2$—.

30. A compound in accordance with claim 25 wherein $R_1$ is cyclopropylmethyl.

31. A compound in accordance with claim 25 wherein $R_1$ is the radical $(CH_3)_2CH(CH_2)$—.

32. A compound of the formula

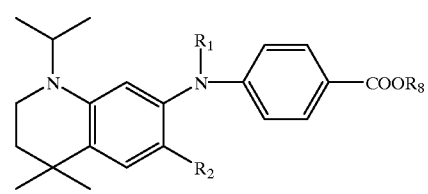

wherein $R_1$ is H, alkyl of 1 to 10 carbons, or cycloalkylalkyl of 4 to 10 carbons;

$R_2$ is H or methyl, and $R_8$ is H, lower alkyl, or a pharmaceutically acceptable salt of said compound.

33. A compound in accordance with claim 32 wherein $R_1$ is hydrogen.

34. A compound in accordance with claim 32 wherein $R_1$ is methyl.

35. A compound in accordance with claim 32 wherein $R_1$ is ethyl.

36. A compound in accordance with claim 32 wherein $R_1$ is cyclopropylmethyl.

37. A compound in accordance with claim 32 wherein $R_1$ is the radical $(CH_3)_2CHCH_2$—.

38. A compound in accordance with claim 32 wherein $R_1$ is n-propyl.

* * * * *

UNITED STATES PATENT AND TRADEMARK OFFICE
CERTIFICATE OF CORRECTION

PATENT NO. : 6,127,382
APPLICATION NO. : 09/375846
DATED : October 3, 2000
INVENTOR(S) : Beard et al.

It is certified that error appears in the above-identified patent and that said Letters Patent is hereby corrected as shown below:

Column 3, line 66, delete "5" before the word "consisting".

Column 9, line 24, "usefull" should be --useful--.

Column 11, line 36, delete "often" before the word "of".

Column 15, line 49, "C." should be --C--.

Column 16, top line of Formula 3,

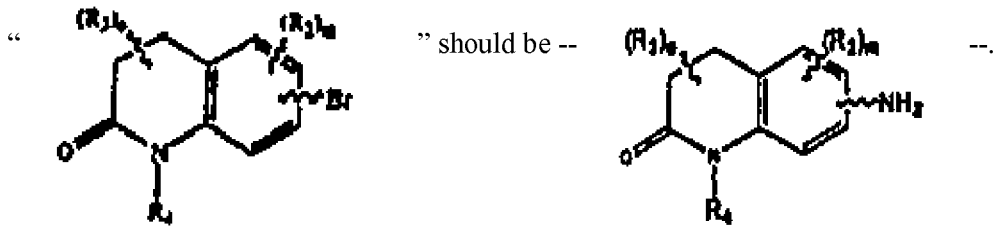

Column 18, line 61, "C." should be --C--.

Column 19, line 13, "C." should be --C--.

Column 20, line 12, "C." should be --C--.

Column 21, second line of Reaction Scheme 5, Structure #19,

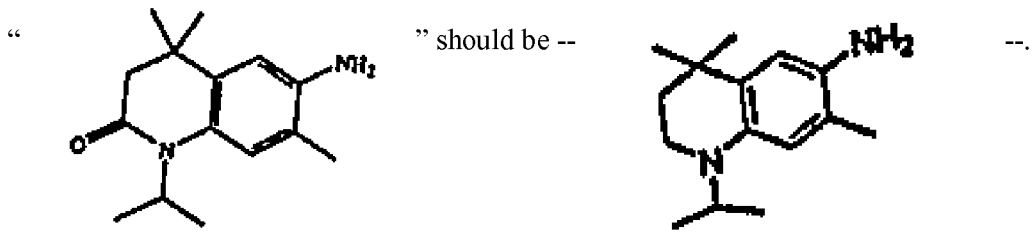

Column 21, below Structure 19, "C." should be --C--.

Column 23, line 6, "C." should be --C--.

Column 23, line 15, "C." should be --C--.

UNITED STATES PATENT AND TRADEMARK OFFICE
CERTIFICATE OF CORRECTION

| | |
|---|---|
| PATENT NO. | : 6,127,382 |
| APPLICATION NO. | : 09/375846 |
| DATED | : October 3, 2000 |
| INVENTOR(S) | : Beard et al. |

It is certified that error appears in the above-identified patent and that said Letters Patent is hereby corrected as shown below:

Column 23, line 22, "C." should be --C--.

Column 23, line 30, "C." should be --C--.

Column 23, line 41, "C." should be --C--.

Column 23, line 55, "C." should be --C--.

Column 23, line 63, "C." should be --C--.

Column 24, line 7, "C." should be --C--.

Column 24, line 55, "C." should be --C--.

Column 24, line 63, "C." should be --C--.

Column 24, line 64, "C." should be --C--.

Column 25, line 7, "C." should be --C--.

Column 25, line 52, "C." should be --C--.

Column 26, line 7, "C." should be --C--.

Column 26, line 57, "C." should be --C--.

Column 27, line 15, "C." should be --C--.

Column 27, line 53, "C." should be --C--.

Column 28, line 20, "C." should be --C--.

Column 28, line 22, "C." should be --C--.

Column 28, line 23, "C." should be --C--.

Column 28, line 36, "1 2,3,4" should be --1,2,3,4--.

Column 28, line 46, "C." should be --C--.

UNITED STATES PATENT AND TRADEMARK OFFICE
CERTIFICATE OF CORRECTION

| | |
|---|---|
| PATENT NO. | : 6,127,382 |
| APPLICATION NO. | : 09/375846 |
| DATED | : October 3, 2000 |
| INVENTOR(S) | : Beard et al. |

It is certified that error appears in the above-identified patent and that said Letters Patent is hereby corrected as shown below:

Column 29, line 25, "C." should be --C--.

Column 30, line 3, "C." should be --C--.

Column 30, line 48, "C." should be --C--.

Column 30, line 67, "C." should be --C--.

Column 31, line 4, "C." should be --C--.

Column 31, line 15, "C." should be --C--.

Column 31, line 18, "C." should be --C--.

Column 31, line 34, "C." should be --C--.

Column 31, line 38, "C." should be --C--.

Column 31, line 58, "C." should be --C--.

Column 32, line 15, "C." should be --C--.

Column 32, line 17, "C." should be --C--.

Column 32, line 18, "C." should be --C--.

Column 32, line 40, "C." should be --C--.

Column 33, line 19 "C." should be --C--.

Column 33, line 63, "C." should be --C--.

Column 34, line 43, "C." should be --C--.

Column 35, line 15, "1 2,3,4" should be --1,2,3,4--.

Column 35, line 23, "C." should be --C--.

Column 35, line 45, "C." should be --C--.

UNITED STATES PATENT AND TRADEMARK OFFICE
CERTIFICATE OF CORRECTION

| | |
|---|---|
| PATENT NO. | : 6,127,382 |
| APPLICATION NO. | : 09/375846 |
| DATED | : October 3, 2000 |
| INVENTOR(S) | : Beard et al. |

It is certified that error appears in the above-identified patent and that said Letters Patent is hereby corrected as shown below:

Column 35, line 61, "C." should be --C--.

Column 35, line 63, "C." should be --C--.

Column 36, line 16, "C." should be --C--.

Column 36, line 17, "C." should be --C--.

Column 36, line 34, "C." should be --C--.

Column 36, line 35, "C." should be --C--.

Column 36, line 59, "C." should be --C--.

Column 37, line 21, "C." should be --C--.

Column 38, line 32, "C." should be --C--.

Column 38, line 50, "1 2,3,4" should be --1,2,3,4--.

Column 38, line 57, "C." should be --C--.

Column 39, line 9, "Isolpropyl" should be --Isopropyl--.

Column 39, line 16, "C." should be --C--.

Column 39, line 42, "C." should be --C--.

Column 39, line 59, "C." should be --C--.

Column 39, line 61, "C." should be --C--.

Column 40, line 9, "3 4" should be --3,4--.

Column 40, line 15, "C." should be --C--.

Column 40, line 16, "C." should be --C--.

UNITED STATES PATENT AND TRADEMARK OFFICE
CERTIFICATE OF CORRECTION

| | | |
|---|---|---|
| PATENT NO. | : 6,127,382 | |
| APPLICATION NO. | : 09/375846 | |
| DATED | : October 3, 2000 | |
| INVENTOR(S) | : Beard et al. | |

It is certified that error appears in the above-identified patent and that said Letters Patent is hereby corrected as shown below:

Column 40, line 35, "C." should be --C--.

Column 40, line 36, "C." should be --C--.

Column 40, line 37, "C." should be --C--.

Column 40, line 59, "C." should be --C--.

Column 41, line 20, "C." should be --C--.

Column 41, line 29, insert --,-- after "s".

Column 42, line 28, "C." should be --C--.

Column 42, line 48, "C." should be --C--.

Column 43, line 1, "C." should be --C--.

Column 43, line 23, "C." should be --C--.

Signed and Sealed this

Seventeenth Day of April, 2007

JON W. DUDAS
*Director of the United States Patent and Trademark Office*